(12) United States Patent
Hulan et al.

(10) Patent No.: US 12,002,576 B2
(45) Date of Patent: Jun. 4, 2024

(54) SYSTEMS AND METHODS FOR UPDATING FIRMWARE OF MEDICAL DEVICES WHILE MINIMIZING CLINICAL IMPACT

(71) Applicant: CareFusion 303, Inc., San Diego, CA (US)

(72) Inventors: Greg T. Hulan, Poway, CA (US); Aron Weiler, San Diego, CA (US); Karthi Rajendran, San Diego, CA (US); Gregory Borges, San Diego, CA (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

(21) Appl. No.: 16/926,497

(22) Filed: Jul. 10, 2020

(65) Prior Publication Data
US 2021/0020306 A1    Jan. 21, 2021

Related U.S. Application Data

(60) Provisional application No. 62/874,445, filed on Jul. 15, 2019.

(51) Int. Cl.
*G16H 40/40* (2018.01)
*G06F 8/65* (2018.01)

(52) U.S. Cl.
CPC .............. *G16H 40/40* (2018.01); *G06F 8/65* (2013.01)

(58) Field of Classification Search
CPC ................................ G16H 40/40; G06F 8/65
(Continued)

(56) References Cited

U.S. PATENT DOCUMENTS 5,713,856 A    2/1998 Eggers et al.
9,889,257 B2 *  2/2018 Mastrototaro ...... A61M 5/1452
(Continued)

FOREIGN PATENT DOCUMENTS

EP      3425505 A1    1/2019
JP    2007299169 A   11/2007
(Continued)

OTHER PUBLICATIONS

Lorengel et al, "Safety and Security for Medical Devices: Analysis and Implementation of a Secure Software Update for Embedded Systems", 2017, [Online], pp. 1-2, [Retrieved from internet on Sep. 8, 2023], <chrome-extension://efaidnbmnnnibpcajpcglclefindmkaj/http://yra-medtech.de/daten_medtech/dokument> (Year: 2017).*
(Continued)

*Primary Examiner* — S. Sough
*Assistant Examiner* — Zengpu Wei
(74) *Attorney, Agent, or Firm* — Morgan, Lewis & Bockius LLP

(57) ABSTRACT

Systems and methods for updating firmware of medical devices while minimizing clinical impact are described. A method includes receiving, by a control module of a patient care device, a new configuration package, including firmware for the control module and/or a first functional module of the patient care device, storing the new configuration package in a first memory bank of the control module, wherein a second configuration package comprising a current version of firmware for at least one of the control module and the first functional module is currently stored in a second memory bank of the control module, determining whether the new configuration package includes a new version of the firmware, and when a new version is included, transmitting the new version to the first functional module, for storage in a different memory bank than a memory bank
(Continued)

currently storing a firmware currently used by the first functional module.

28 Claims, 24 Drawing Sheets

(58) Field of Classification Search
USPC .......................................................... 717/172
See application file for complete search history.

(56) References Cited

U.S. PATENT DOCUMENTS

| | | | |
|---|---|---|---|
| 9,971,871 B2 | 5/2018 | Arrizza et al. | |
| 10,025,909 B2 | 7/2018 | Gray et al. | |
| 2003/0095648 A1 | 5/2003 | Kaib et al. | |
| 2003/0221015 A1* | 11/2003 | Basso | H04L 41/0896 709/234 |
| 2005/0148869 A1* | 7/2005 | Masuda | A61M 5/1456 600/432 |
| 2008/0163190 A1* | 7/2008 | Shirota | G06F 8/65 717/170 |
| 2009/0271507 A1* | 10/2009 | Kodimer | G06F 8/65 709/224 |
| 2010/0313105 A1* | 12/2010 | Nekoomaram | H04L 67/10 717/171 |
| 2011/0289497 A1* | 11/2011 | Kiaie | G01N 33/48792 717/171 |
| 2013/0205290 A1* | 8/2013 | Kroell | G16H 40/40 717/171 |
| 2015/0121358 A1* | 4/2015 | Nekoomaram | G08B 29/24 717/170 |
| 2015/0178061 A1* | 6/2015 | Wang | G06F 8/61 717/172 |
| 2015/0199192 A1 | 7/2015 | Borges et al. | |
| 2015/0199485 A1* | 7/2015 | Borges | G16H 40/63 600/323 |
| 2016/0129185 A1 | 5/2016 | Ludolph | |
| 2018/0341476 A1* | 11/2018 | Kitao | H04L 67/34 |
| 2019/0201114 A1* | 7/2019 | Shelton, IV | G16H 40/60 |
| 2020/0027541 A1* | 1/2020 | Xavier | G06F 9/542 |
| 2020/0035358 A1* | 1/2020 | Williams | A61G 7/05 |
| 2022/0344023 A1* | 10/2022 | Xavier | G16H 40/20 |

FOREIGN PATENT DOCUMENTS

| | | |
|---|---|---|
| KR | 20130111852 A | 10/2013 |
| KR | 20140052735 A | 5/2014 |

OTHER PUBLICATIONS

Schaeffer et al."Insulin Pumps and Remote Software Updates: A New Way Forward", 2016, [Online], pp. 453-456, [Retrieved from internet on Dec. 7, 2023], <chrome-extension://efaidnbmnn-nibpcajpcglclefindmkaj/https://journals.sagepub.com/doi/pdf/10.1177/1932296815604857> (Year: 2016).*

International Search Report and Written Opinion for Application No. PCT/US2020/042015, dated Oct. 22, 2020, 13 pages.

Korean Office Action for Application No. 10-2022-7004658, dated Nov. 23, 2023, 12 pages including translation.

Canadian Office Action for Application No. 3147234, dated Feb. 27, 2024, 7 pages.

Korean Office Action for Application No. 10-2022-7004658, dated Jan. 31, 2024, 5 pages including translation.

* cited by examiner

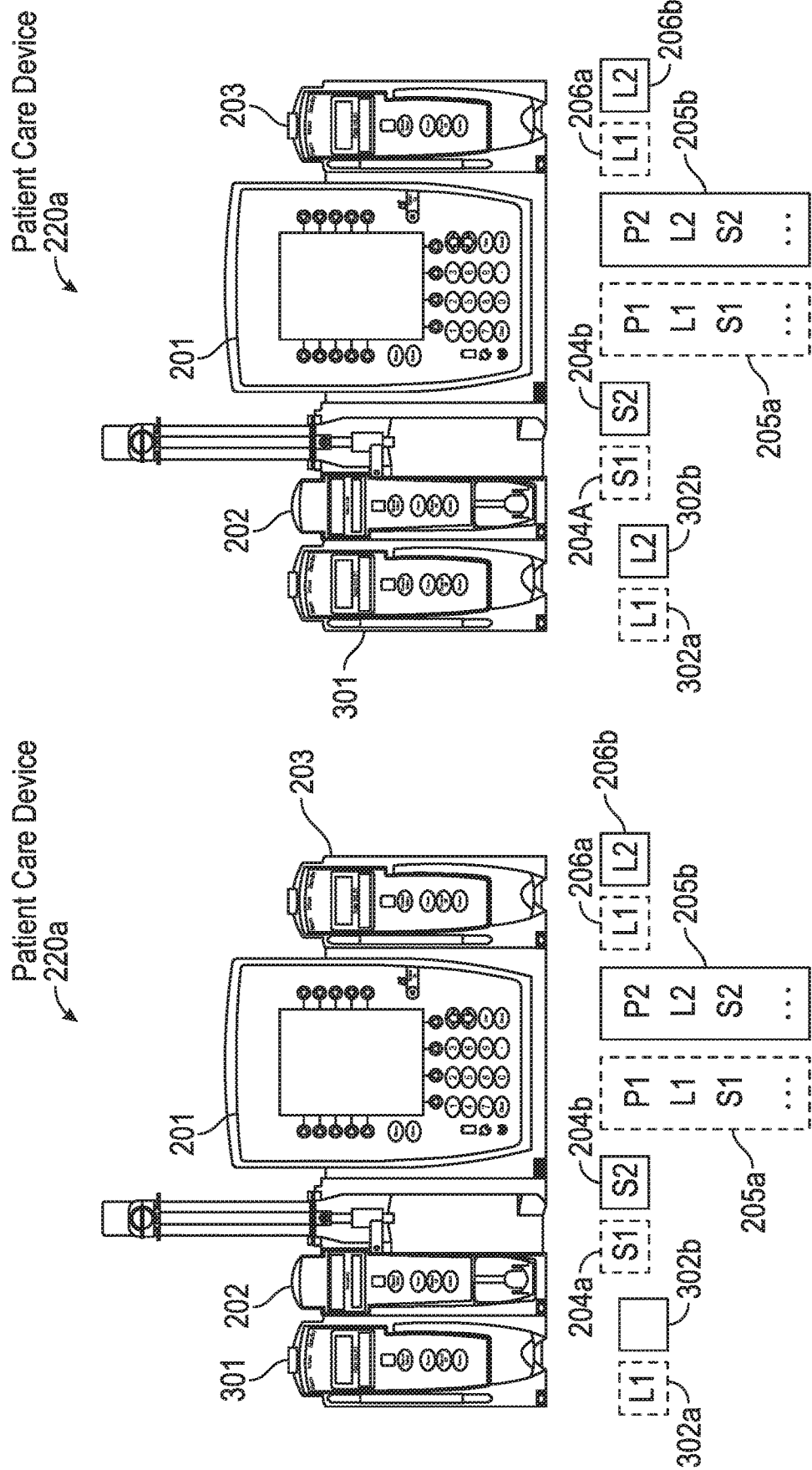

Manage Firmware Deployments

| | Configuration Zone | | | | | | |
|---|---|---|---|---|---|---|---|
| | System Configuration | | | | | | |
| Actions ⌄ | Permissions and Roles | | | Search all firmware deployments 🔍 | | | |

| Configuration Zone / Description ⬥ | Firmware Package ⬥ | Model 9200 (PCU) | Model 9210 (LVP) | Transferred ⬥ to PCU | Active ⬥ on PCU | Deployed By ⬥ | Deployed ⬥ |
|---|---|---|---|---|---|---|---|
| ☐ North<br>UT North Campus | 1.1.5.11 | 3.3.3.3 | 1.2.1.2 | HOLD | HOLD | Brian Sullivan | 00/00/2018<br>03:50 pm |
| ☐ Southwest<br>UT Main Univ Hospital | 1.1.5.11 | 3.3.3.3 | 1.2.1.2 | 80%<br>80/100 | 80%<br>80/100 | Brian Sullivan | 00/00/2018<br>12:22 pm |
| ☐ MHMC East<br>MHMC Hospital East | 1.1.5.40 | 3.3.3.3 | 1.2.1.2 | 80%<br>80/100 | 80%<br>80/100 | Brian Sullivan | 00/00/2018<br>05:03 pm |
| ☐ MHMC North<br>MHMC Hospital North | 1.1.4.10 | 2.2.2.2 | 1.2.1.2 | 50%<br>50/100 | 50%<br>50/100 | Brian Sullivan | 00/00/2018<br>07:59 pm |
| ☐ MHMC South<br>MHMC Hospital South | 1.1.3.1 | 2.2.2.2 | 1.2.1.2 | 40%<br>40/100 | 40%<br>40/100 | Brian Sullivan | 00/00/2018<br>01:34 pm |

FIG. 4A

SYSTEMS AND METHODS FOR UPDATING FIRMWARE OF MEDICAL DEVICES WHILE MINIMIZING CLINICAL IMPACT

CROSS REFERENCE TO RELATED APPLICATIONS

This application claims the benefit of priority as a non-provisional of U.S. Application Ser. No. 62/874,445, entitled "SYSTEMS AND METHODS FOR UPDATING FIRMWARE OF MEDICAL DEVICES WHILE MINIMIZING CLINICAL IMPACT," filed on Jul. 15, 2019, the entirety of which is incorporated herein by reference.

TECHNICAL FIELD

This application relates generally to updating firmware of medical devices, such as infusion devices.

BACKGROUND

A healthcare facility, such as a hospital, generally include a large number of medical devices. Each medical device executes a particular version of a firmware. Due to the large number of medical devices within a healthcare facility, maintenance of the medical devices and ensuring each medical device is compatible with other medical devices of the healthcare facility may be burdensome and time consuming for technicians of the healthcare facility. Furthermore, incompatibility between medical devices may cause medical devices to be unusable for a significant amount of time increasing operational costs of a medical facility.

SUMMARY

In one or more implementations, a computer-implemented method includes receiving, by a control module of a patient care device, a new configuration package, wherein the new configuration package comprises new versions of firmware for at least one of the control module and a first functional modules of the patient care device. The method includes storing, by the control module, the new configuration package in a first memory bank of the control module, wherein a second configuration package is stored in a second memory bank of the control module when the new configuration package is received, and wherein the second configuration package comprises a current version of firmware for at least one of the control module and the first functional modules. The method includes determining, by the control module, based on information associated with the new configuration package, whether the new configuration package includes a new version of the firmware for the first functional module connected to the control module. The method includes, based on determining that the new version of firmware is included, transmitting, by the control module, the new version of firmware to the first functional module, wherein the new version is stored on the first functional module in a different memory bank than a memory bank currently storing a firmware currently used by the first functional module. Other aspects include corresponding systems, apparatus, and computer program products for implementation of the method.

In one or more implementations, a system includes a first functional module, and a control module. The control module comprising a memory and one or more processors configured to execute instructions stored on the memory to cause the control module to receive a new configuration package, wherein the new configuration package comprises new versions of firmware for at least one of the control module and the first functional module. The one or more processors configured to execute instructions to cause the control module to store the new configuration package in a first memory bank of the control module, wherein a second configuration package is currently stored in a second memory bank of the control module when the new configuration package is received, and wherein the second configuration package comprises a current version of firmware for at least one of the control module and the first functional module. The one or more processors configured to execute instructions to cause the control module to determine whether the new configuration package includes a new version of the firmware for the first functional module connected to the control module. The one or more processors configured to execute instructions to cause the control module to, when the new version of firmware is included, transmit the new version of firmware to the first functional module, wherein the new version is stored on the first functional module in a different memory bank than a memory bank currently storing a firmware currently used by the first functional module.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

For a better understanding of the various described implementations, reference should be made to the Detailed Description below, in conjunction with the following drawings. Like reference numerals refer to corresponding parts throughout the figures and description.

FIGS. 3A-FIG. 3C depict an example of transmission of a version for firmware in a patient care device, according to illustrative implementations.

FIGS. 4A-FIG. 4B depict an example of transmission of an activation signal and execution of corresponding version of firmware, according to illustrative implementations.

DETAILED DESCRIPTION

Figure 1A:
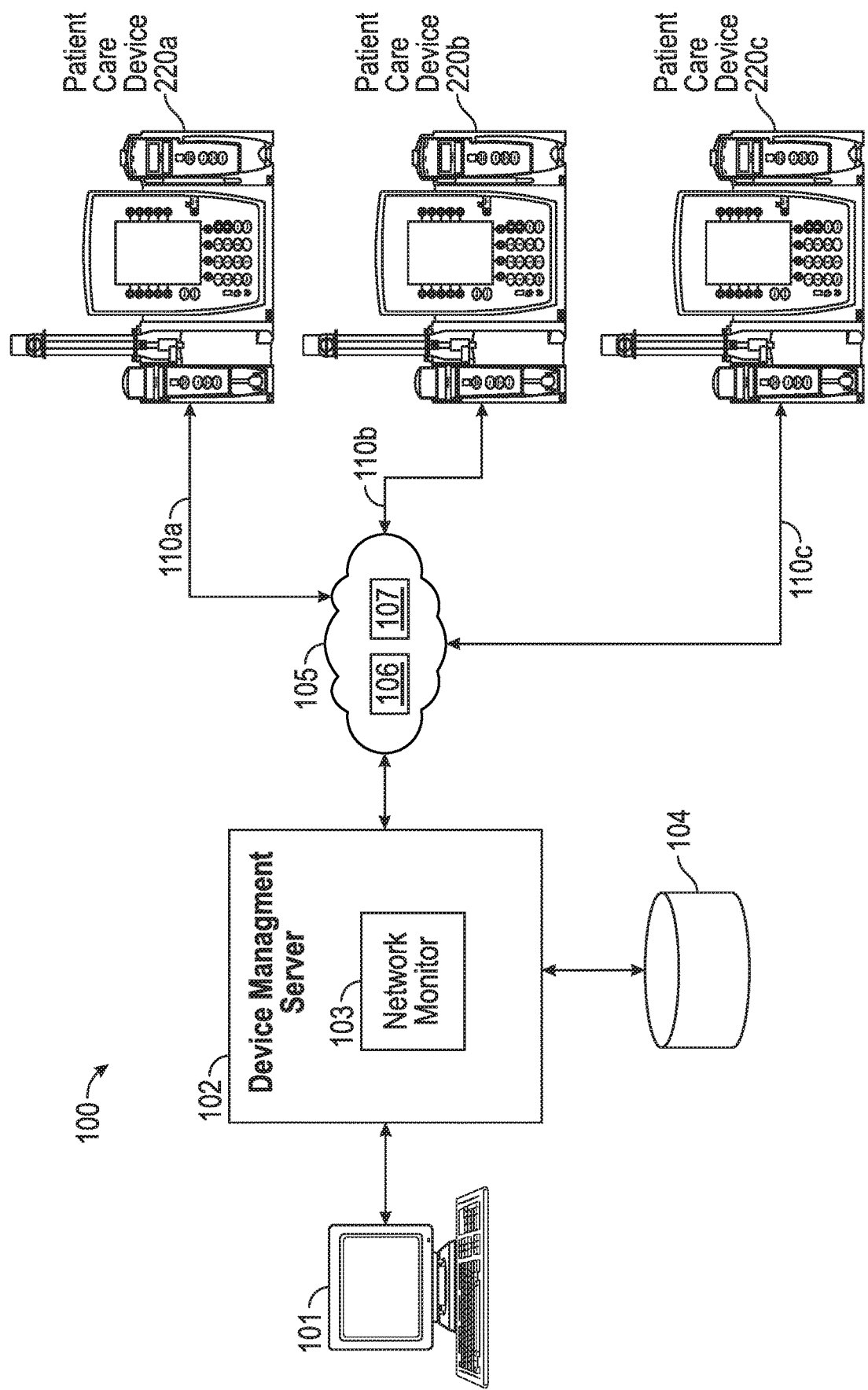
FIGS. 1A-FIG. 1C depict an example of an institutional patient care system of a healthcare organization, according to illustrative implementations.

The detailed description set forth below is intended as a description of various configurations of the subject disclosure and is not intended to represent the only configurations in which the subject disclosure may be practiced. The appended drawings are incorporated herein and constitute a part of the detailed description. The detailed description includes specific details for the purpose of providing a thorough understanding of the subject disclosure. However, it will be apparent to those skilled in the art that the subject disclosure may be practiced without these specific details. In some instances, structures and components are shown in block diagram form in order to avoid obscuring the concepts of the subject disclosure. Like components are labeled with identical element numbers for ease of understanding.

The terminology used in the description of the various implementations described herein is for the purpose of describing particular implementations only and is not intended to be limiting. As used in the description of the various described implementations and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed terms. It will be further understood that the terms "includes," "including," "comprises," and/or "comprising" when used in the specification, specify the presence of stated features, steps, operations, elements, and/or components, but do not preclude the presence or addition of one or more other features, steps, operations, elements, components, and/or groups thereof.

The present disclosure relates in general to updating medical devices while minimizing clinical impact during the update process. Medical devices may be initially configured during manufacturing or by a supplier to allow for communication with other medical devices (e.g., via a network) of a medical facility. Over a lifetime of a medical device, updates to the configuration of the medical devices may be necessary. However, installing the updates on the medical devices may be time consuming and may cause the medical devices to be unavailable for a period of time, which may interfere with daily operations of a medical facility. The systems and techniques described herein allow for a deployment of a configuration package to a medical device, such as a multi-channel medical system. The deployable configuration package may include firmware or a firmware update for one or more medical devices in communication with each other, or with other external systems or non-updated medical devices. Also, a configuration package for a multi-channel medical system may include firmware for each channel of a medical system, or for each module device connected to the medical system (or associated device controller). Additional details of the configuration package and the updating the medical devices are described herein with reference to FIGS. 1A-10.

FIG. 1A depicts an example of an institutional patient care system 100 of a healthcare organization, according to aspects of the subject technology. In FIG. 1A, patient care devices 220a, 220b, 220c, collectively referred to as PCD 220, may include various medical devices such as an infusion pump, a vital signs monitor, a medication dispensing device (e.g., cabinet, tote), a medication preparation device, an automated dispensing device, a module coupled with one of the aforementioned (e.g., a syringe pump module configured to attach to an infusion pump), or other similar devices. Each PCD 220 is connected to an internal healthcare network 105 by a transmission channel, such as transmission channels 110a, 110b, 110, collectively referred to as transmission channel 110. A transmission channel 110 may be or include one or more wired or wireless transmission channel, for example an 802.11 wireless local area network (LAN). In some implementations, network 105 also includes computer systems located in various departments throughout a hospital. For example, network 105 of FIG. 1A optionally includes computer systems associated with an admissions department, a billing department, a biomedical engineering department, a clinical laboratory, a central supply department, one or more unit station computers and/or a medical decision support system. As described further below, network 105 may include discrete subnetworks. In the depicted example, network 105 includes a device network 106 by which patient care devices 220 (and other devices) communicate in accordance with normal operations, and a provisioning network 107 by which the devices may connect upon start up to load certain parameters required for operation within the institutional patient care system 100 environment.

Additionally, institutional patient care system 100 may incorporate a separate device management server 102, the function of which will be described in more detail below. Moreover, although the device management server 102 is shown as a separate server, the functions and programming of the device management server 102 may be incorporated into another computer, such as, for example, a hospital information system server, if such is desired by engineers designing the institution's information system. Institutional patient care system 100 may further include one or multiple device terminals 101 for connecting and communicating with device management server 102. Device terminals 101 may include personal computers, personal data assistances, mobile devices such as laptops, tablet computers, augmented reality devices, or smartphones, configured with software for communications with device management server 102 via network 105.

Figure 1B:
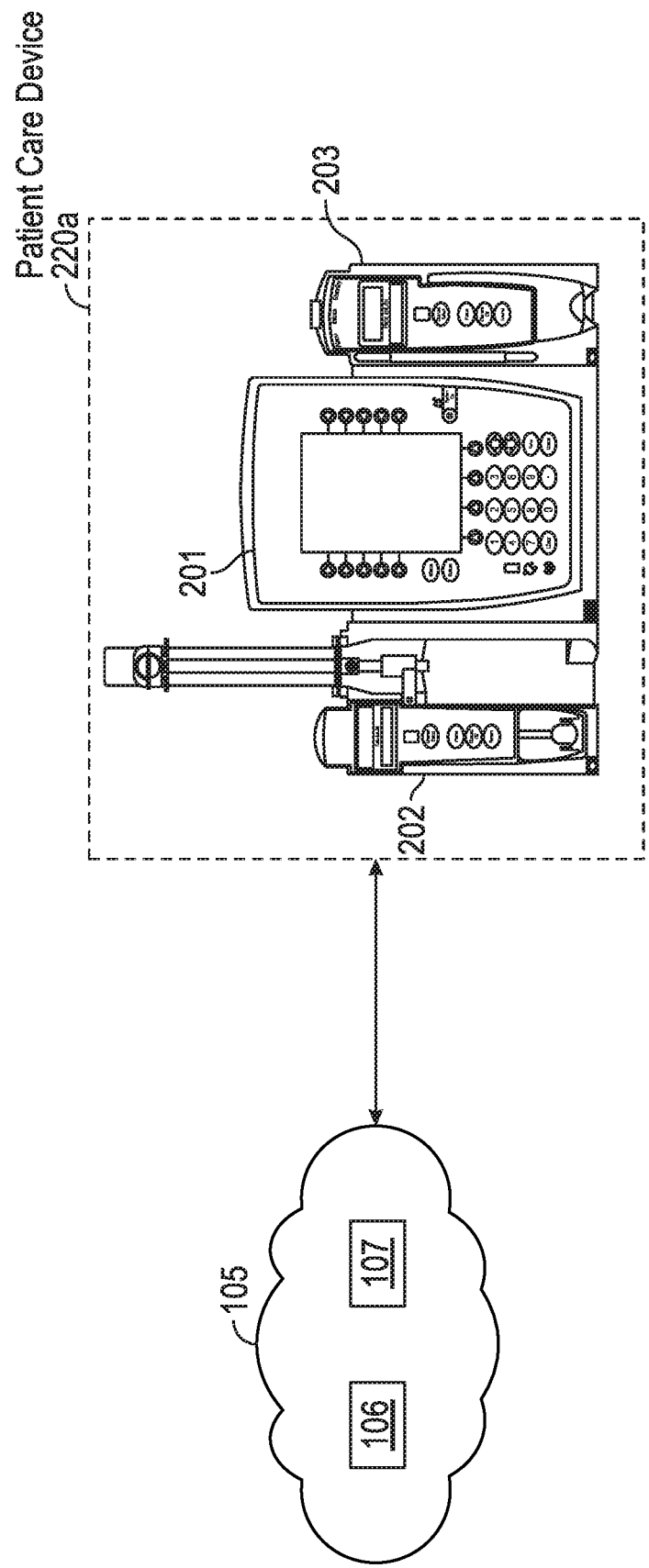

A patient care device 220 includes a system for providing patient care, such as that described in U.S. Pat. No. 5,713,856 to Eggers et al., which is incorporated herein by reference for that purpose. Patient care devices 220 may include one or more functional modules. Examples of functional modules may include or incorporate pumps, physiological monitors (e.g., heart rate, blood pressure, ECG, EEG, pulse oximeter, and other patient monitors), therapy devices, and other drug delivery devices may be utilized according to the teachings set forth herein. For example, as shown in FIG. 1B, patient care devices 220, such as patient care device 220a, may include a functional module 202

Figure 1C:
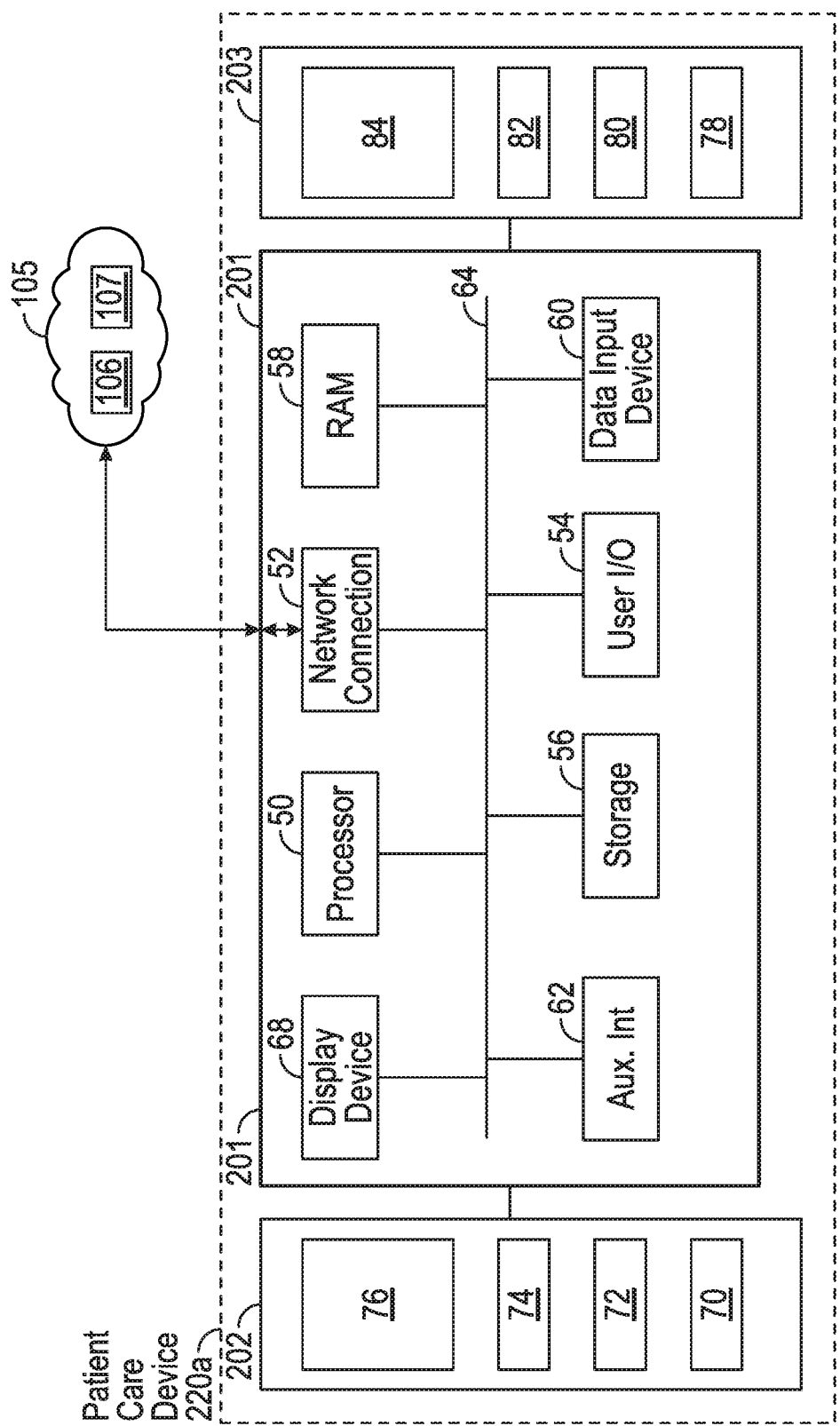

(e.g., a pump), another functional module 203 (e.g., drug delivery device). In the depicted example shown in FIG. 1B, patient care devices 220, may include a control module 201, also referred to as interface unit 201, connected to one or more functional modules 202, 203. Additional details of PCD 220 are shown in FIG. 1C Turning now to FIG. 1C, there is shown a block diagram of a PCD 220. As described above, a PCD 220, such as PCD 220a, may include a control module 201 connected to functional modules 202, 203. Control module 201 may include a central processing unit (CPU) 50 connected to a memory, for example, random access memory (RAM) 58, and one or more interface devices such as user interface device 54, a coded data input device 60, a network connection 52, and an auxiliary interface 62 for communicating with additional modules or devices. Control module 201 may include a main non-volatile storage unit 56, such as a hard disk drive and/or a non-volatile flash memory, for storing software and data, and one or more internal buses 64 for interconnecting the aforementioned elements.

In some implementations, user interface device 54 is a touch screen for displaying information to a user and allowing a user to input information by touching defined areas of the screen. User interface device 54 could include additional or alternative means for displaying and inputting information, such as a monitor, a printer, a keyboard, softkeys, a mouse, a track ball, and/or a light pen. Data input device 60 may be a bar code reader capable of scanning and interpreting data printed in bar coded format. Data input device 60 can be an additional or alternative device for entering coded data into a computer, such as a device(s) for reading a magnetic strips, radio-frequency identification (RFID) devices whereby digital data encoded in RFID tags or smart labels (defined below) are captured by the data input device 60 via radio waves, PCMCIA smart cards, radio frequency cards, memory sticks, CDs, DVDs, or other analog or digital storage media directly or indirectly accessible by the data input device 60. Other examples of data input device 60 include a voice activation or recognition device or a portable personal data assistant (PDA). Depending upon the types of interface devices used, user interface device 54 and data input device 60 may be the same device. Although data input device 60 is shown in FIG. 1C to be disposed within interface unit 14, it is recognized that data input device 60 may be integral within pharmacy system 34 or located externally and communicating with pharmacy system 34 through an RS-232 serial interface or other appropriate communication means. Auxiliary interface 62 may be an RS-232 communications interface, however other means for communicating with a peripheral device such as a printer, patient monitor, infusion pump or other medical device may be used without departing from the subject technology. Additionally, data input device 60 may be a separate functional module, such as functional modules 202 and 203, and may be configured to communicate with control module 201, or another system on the network, using suitable programming and communication protocols.

Network connection 52 may be a wired or wireless connection, such as by Ethernet, WiFi, BLUETOOTH, an integrated services digital network (ISDN) connection, a digital subscriber line (DSL) modem or a cable modem. A direct or indirect network connection may be used, including, but not limited to a telephone modem, an MIB system, an RS232 interface, an auxiliary interface, an optical link, an infrared link, a radio frequency link, a microwave link or a WLANS connection or other wireless connection. As shown in FIG. 1C, patient care device 220 may be communicatively coupled to a network 105 via network connection 52.

Functional modules 202, 203 may be implemented as devices for providing care to a patient or for monitoring patient condition. In some implementations, as shown in FIG. 1C, the functional modules 202, 203 may be an infusion pump module such as an intravenous infusion pump module, a large volume pump module, a syringe module, and the like, for delivering medication or other fluid to a patient. For the purposes of this discussion, functional module 202 is a large volume pump module, and functional module 203 may be a patient treatment or monitoring device including, but not limited to, an infusion pump, a syringe pump, a fluid pump, a PCA pump, an epidural pump, an enteral pump, a blood pressure monitor, a pulse oximeter, an EKG monitor, an EEG monitor, a heart rate monitor or an intracranial pressure monitor or the like. In some implementations, a patient care device 220 may include additional functional modules (not shown here) such as a printer, scanner, a bar code reader, and/or other peripheral input, output, and/or input/output device related to the provisioning of care to a patient in acute or non-acute settings.

Each functional module 202, 203 communicates directly or indirectly with control module 201, with control module 201 providing overall monitoring and control of PCD 220a. Functional modules 202, 203 may be connected physically and electronically in serial fashion to one or both ends of control module 201 as shown in FIG. 1C, or as detailed in Eggers et al. However, it is recognized that there are other means for connecting functional modules with the interface unit that may be utilized without departing from the subject technology. It will also be appreciated that devices such as pumps or patient monitoring devices that provide sufficient programmability and connectivity may be capable of operating as stand-alone devices and may communicate directly with the network without connected through a separate interface unit or control module 201. As described above, additional medical devices or peripheral devices may be connected to patient care devices 220 through one or more auxiliary interfaces 62.

Each functional module 202, 203 may include module-specific components 76, 84, a microprocessor 70, 78, a volatile memory 72, 80, and a nonvolatile memory 74, 82 for storing information and/or data. It should be noted that while two functional modules are shown in FIG. 1C, additional or alternative devices may be connected directly or indirectly to control module 201. The number and type of functional modules described herein are intended to be illustrative, and in no way limit the scope of the subject technology. Module-specific components 76, 84 include components for operation of a particular module, such as a pumping mechanism for infusion pump module 202, and 203, respectively.

While each functional module may be configured of a least some level of independent operation, control module 201 may be configured to monitor and control overall operation of a PCD 220, such as PCD 220a. For example, as will be described in more detail below, control module 201 provides programming instructions to the functional modules 202, 203 and monitor the status of each module.

Patient care devices 220 may be configured to operate in several different modes, or personalities, with each mode or personality defined by a firmware and/or stored information and/or software packages. In some implementations, particular stored information may be updated or a software package may be selected based on patient-specific information such as patient location, age, physical characteristics, or medical characteristics. Medical characteristics include, but are not limited to, patient diagnosis, treatment prescription, medical history, medical records, patient care provider identification, physiological characteristics or psychological characteristics. As used herein, patient-specific information may also include care provider information (e.g., physician identification) or a location of a PCD 220 in the care facility (e.g., hospital) or care facility computer network. Patient care information may be entered through interface device 52, 54, 60 or 62, and may originate from a device attached to network 105, such as, for example, a pharmacy server, admissions server, laboratory server, and the like.

Data to and from the various data sources can be converted into network-compatible data with existing technology, and movement of the information between the medical device and network can be accomplished by a variety of means. For example, patient care devices 202 and network 105 may communicate via automated interaction, manual interaction or a combination of both automated and manual interaction. Automated interaction may be continuous or intermittent and may occur through direct network connection 54 (as shown in FIG. 1C), or through RS232 links, MIB systems, RF links such as BLUETOOTH, IR links, WLANS, digital cable systems, telephone modems or other wired or wireless communication means. Manual interaction between patient care devices 220 and network 105 involves physically transferring, intermittently or periodically, data between systems using, for example, user interface device 54, coded data input device 60, bar codes, computer disks, portable data assistants, memory cards, or other media for storing data. The communication means in various aspects is bidirectional with access to data from as many points of the distributed data sources as possible. Decision-making can occur at a variety of places within network 105. For example, and not by way of limitation, decisions can be made in device management server 102, network monitor 103, and/or within patient care device 220 itself.

Each control module of a PCD 220, such as control module 201, may be configured to store multiple versions of firmware in memory. Each control module of a PCD 220 may be configured to execute a first version of a firmware stored in a first portion of a memory, such as storage device 56, while a second version of the firmware may be stored in a second portion of memory. A portion of a memory may be referred to herein as a "memory bank." Each firmware stored in a control module of PCD 220 may be configured to be readily executable, and a control module may be configured to switch between different versions of firmware stored in memory banks. For example, the control module of a PCD 220, in response to receiving a command, may be configured to switch from executing a first version of firmware stored in a first memory bank to executing a second version of firmware stored in a second memory bank. Similarly, each functional module of a PCD 220, such as a functional module 202, 203, may be configured to store multiple versions of firmware in a memory, such as non-volatile memory 74, 82. A control module of a PCD 220, such as control module 201, may be configured to transmit a version of firmware to one or more functional modules of the PCD 220, and the functional modules of the PCD 220 store the received version of firmware in one of the memory banks of the functional modules. The functional modules of the PCD 220 may be configured to switch between different versions of the firmware stored in the memory banks in response to receiving a command from the control module of the PCD 220.

Figure 2A:
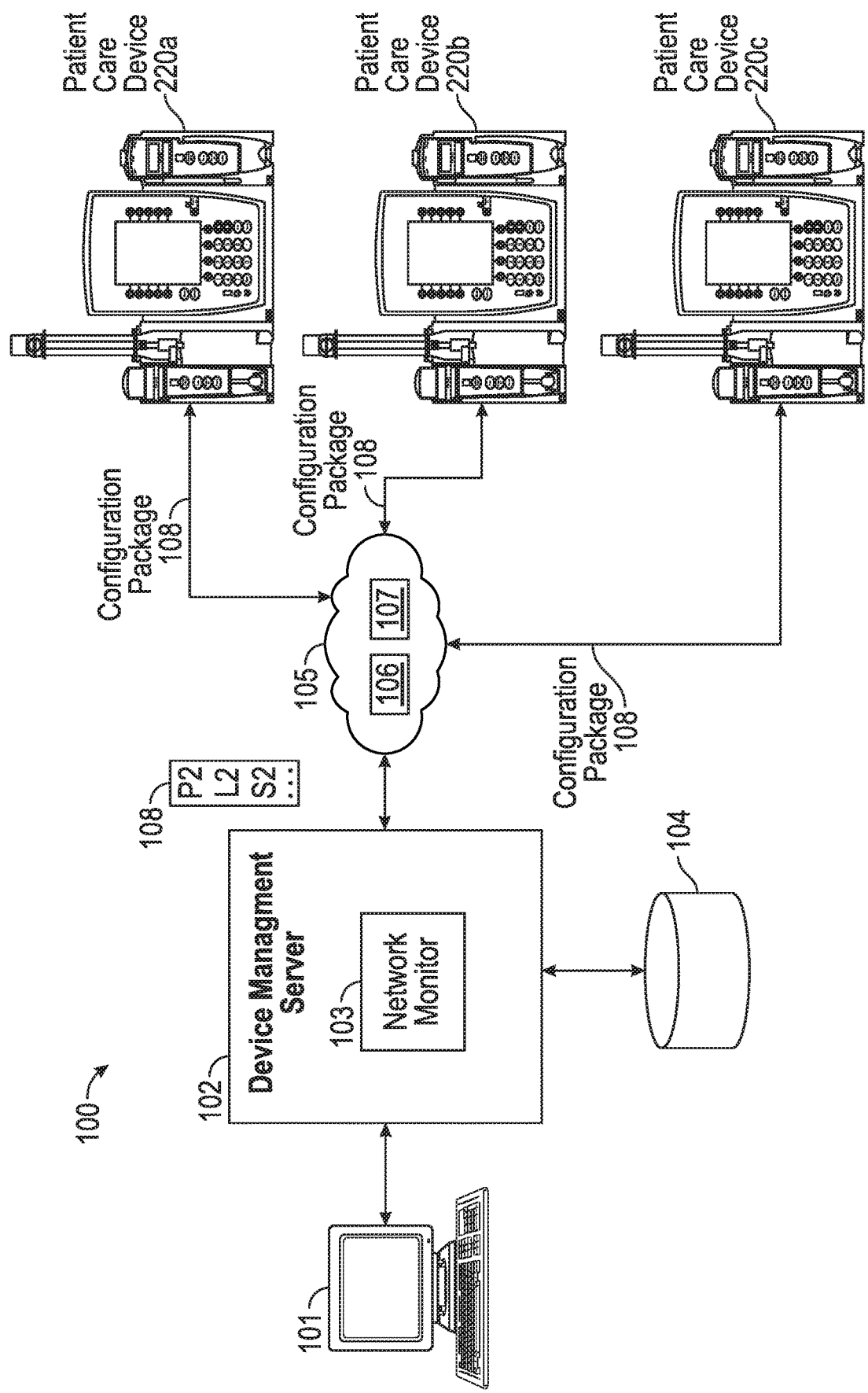
FIGS. 2A-FIG. 2D depict an example of transmission of a configuration package between various elements of an institutional patient care system, according to illustrative implementations.

As shown in FIGS. 1A and 2A, device management server 102 may be in communication with one or multiple various patient related units 220. Each of the patient related units 220 may provide therapy to a patient or monitor the patient's vital signs or condition, and provide information about the status of the patient and the patient's therapy to the device management server 102. A network monitoring application program 103 provides an interface with the server 102, and thus the assets in communication with the server 102. Using the network application program 103, users such as a pharmacist, nurse, physician and biomedical technician may view the information provided to the server by the various patient care devices 220, and/or monitor the operation of the patient care devices 220. Using such a system, a biomedical technician may transmit a configuration package to the patient care devices 220.

A client-server environment incorporating aspects of the subject technology may include a central server (e.g., device management server 102) that is accessible by at least one client, such as client system 101, via a computer network. In some implementations, the central server may be accessible by at least one local server via a computer network, such as, for example, an Ethernet, wireless network, or the Internet, which may in turn be accessed by a client. A variety of computer network transport protocols including, but not limited to TCP/IP, can be utilized for communicating between the central server, local servers (e.g., hospital information system servers), and client devices configured with a communications capability compatible with the communication protocol used on the network.

The device management server 102 may include or is communicatively coupled to a central database 104. The device management server 102 may ensure that the local servers are running the most recent version of a knowledge base, and also may store patient data and perform various administrative functions including adding and deleting local servers and users to the system. The device management server 102 may also provide authorization before a local server or a PCD 220 can be utilized by a user. The device management server 102 may associate each PCD 220 with a certain configuration zone. As stated previously, in the example integrated systems, patient data and a current operating status of PCDs 220 may be stored on device management server 102, thereby providing a central repository of patient data and operating status of PCDs 220. However, it is understood that operating status of PCDs 220 can be stored on a local server or on local storage media, or on another hospital or institutional server or information system, where it may be accessed through the various elements of the system, such as client server 101, as needed.

In some implementations, local client or medical device may include a client application program that may include a graphical user interface (GUI) and may be configured to communicate device management server 102. For example, a local client or a medical device may include a middle layer program that communicates with central or local servers. In some implementations, program code for the client application program may execute entirely on the local client, or it may execute partly on the local client and partly on the central or local server.

Computer program code for carrying out operations of the subject technology may be written in an object oriented programming language such as, for example, JAVA®, Smalltalk, or C++. However, the computer program code for carrying out operations of the subject technology may also be written in conventional procedural programming languages, such as the "C" programming language, in an interpreted scripting language, such as Perl, or in a functional (or fourth generation) programming language such as Lisp, SML, Forth, or the like. The software may also be written to be compatible with HLA-7 requirements.

Medical devices, such as PCDs 220, incorporating aspects of the subject technology may be equipped with a Network Interface Module (NIM), allowing the medical device to participate as a node in a network. While for purposes of clarity the subject technology will be described as operating in an Ethernet network environment using the Internet Protocol (IP), it is understood that concepts of the subject technology are equally applicable in other network environments, and such environments are intended to be within the scope of the subject technology.

All direct communications with medical devices, such as PCDs 220 operating on a network in accordance with the subject technology may be performed through device management server 102, known as the remote data server (RDS). In accordance with aspects of the subject technology, network interface modules incorporated into medical devices such as, for example, infusion pumps or vital signs measurement devices, ignore network traffic that does not originate from an authenticated RDS. The primary responsibilities of the RDS of the subject technology are to track the location and status of networked medical devices that have NIMs, and maintain open communication channels with them.

Prior to implementation within institutional patient care system 100, patient care devices 220 may be manufactured with default network information for allowing the devices to connect a designated provisioning service for receiving specific configuration information for normal operation within institutional patient care system 100 including, for example, network information and/or security information for connecting to network 105 and to device management server 102.

When patient care devices 220 are received at a healthcare facility of the healthcare organization, an administrator may, via a terminal device 101, create records for the devices in database 104. In this regard, each record may include a unique identification (ID) of a respective device 220 (e.g., a serial number, media access control address, mobile device identifier, device name, and the like). The unique ID may be affixed to the device (e.g., as a printed label or RFID tag) and captured by a scanner device such as a bar code reader or RFID reader device. The record may map the unique ID to the specific configuration information. In some implementations, the unique IDs of the device(s) may be electronically received by device management server 102, for example, via an external network (not shown), such as the Internet or other WAN. Device management server 102 may provide a user interface for acceptance and/or confirmation of the device(s) to receive the configuration packages prior to the configuration package being provided to the medical devices, such as PCDs 220.

In accordance with various implementations, device management server 102 may be responsible for managing access of patient care devices 220 to network systems of the institutional patient care system 100, communications between the various devices over network 105, and routine management of patient care devices 220. In this regard, device management server 102 may provide, via terminal device(s) 101, a user interface for assignment of the one or more device identifiers to one or more security certificates. The security certificates, once installed on the patient care device(s) 220, enable the patient care device(s) to access and communicate with the device management server 102 and/or other devices within institutional patient care system 100.

In some implementations, the user interface provided by the management server 102, may facilitate an assignment of the device identifiers and security certificates to a respective facility within the healthcare organization. In this regard, configuring patient care device(s) 220 to access and communicate with device management server 102 includes configuring patient care device(s) 220 to communicate via network 105 (or transmission channel 110) within the respective facility, with an encrypted security certificate specific to the respective facility. Additional details of a control module and functional modules of a PCD 220 receiving, storing, and executing a version of firmware are described herein with reference to FIGS. 2A-10.

Turning to FIG. 2A, there is shown an example of transmission of a configuration package between various elements of an institutional patient care system. For the purpose of illustrating a clear example, components of the institutional patient care system 100 shown and described with reference to FIGS. 1A-1C are used to describe the transmission of the configuration package.

A user, such as a biomedical technician or an information technology professional, via a device terminal 101 may transmit a configuration package, such as configuration package 108, to one or more PCDs 220 via the device management server 102. Each configuration package 108 may include a firmware for each component of a PCD 220. For example, the configuration package may include a firmware for a control module and/or a functional module of a PCD 220. Each firmware included in the configuration package may be configured and tested to be compatible with every other firmware included in the configuration package. According to various implementations, a respective configuration package may include various settings (e.g., parameters) for operating PCD 220 or a module connected thereto. For example, the configuration package may include operational parameters such as a default infusion rate or infusion parameter limits.

In some implementations, configuration packages may be transmitted to the PCDs 220 based on a configuration zone associated with the PCDs 220. For example, PCD 220a and PCD 220b may be associated with a first configuration zone, and PCD 220c may be associated with a second configuration zone. In this regard, the firmware and/or settings of a configuration package may be specific to the configuration zone. According to various implementations, a configuration zone may be associated with a predetermined geographical location or care area within a medical facility. In this regard, the firmware and/or settings of the configuration package may reflect operation of the target device within the particular geographical location or care area of the facility. For example, a first configuration package may include firmware and/or settings specific to emergency rooms, while a second configuration package may include firmware and/or settings specific to an intensive care unit (ICU), while another configuration package may include general firmware and/or settings for non-emergency or non-ICU related patient use. As shown in FIG. 2A, a device management server 102 may transfer a configuration package 108 to PCDs 220 via network 105 and/or communication channels 110.

Figure 2C:
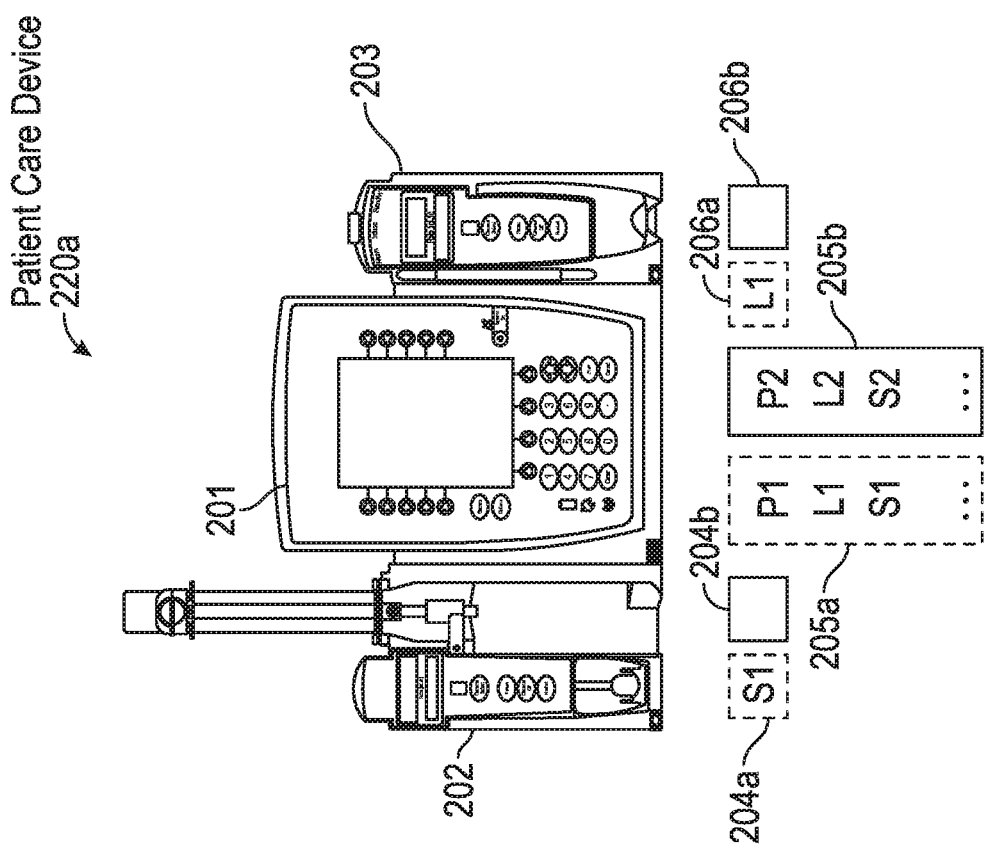
Figure 2B:
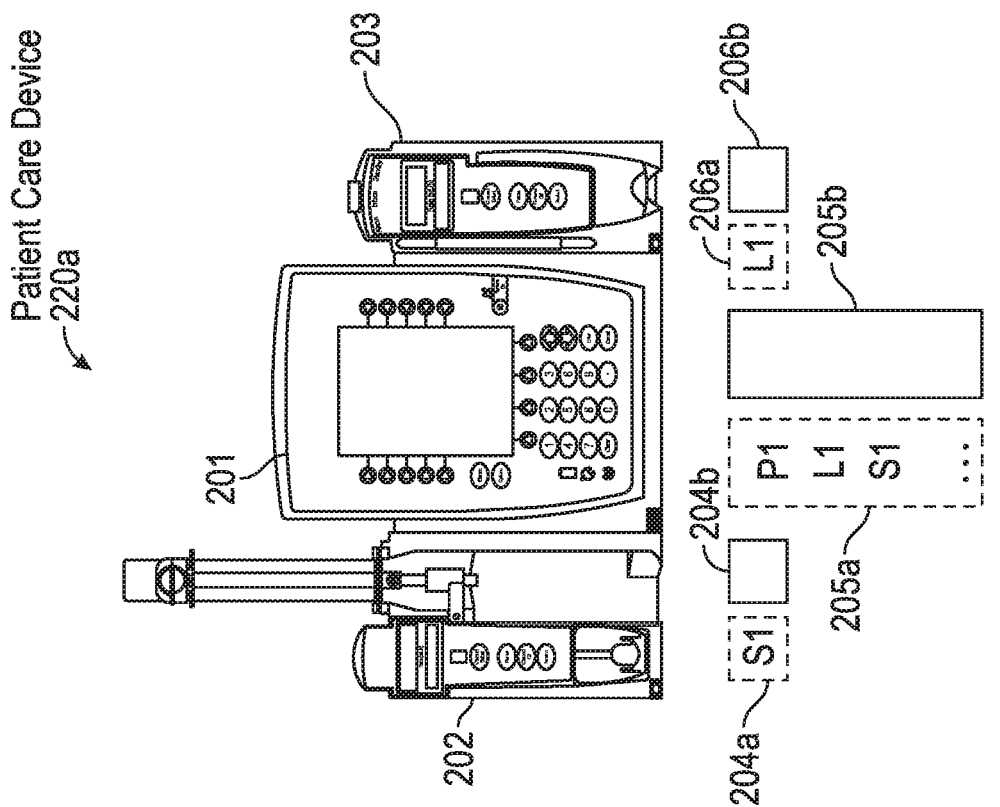

Components of a patient care device 220, such as PCD 220a, may be executing a version of firmware associated with first configuration package. For example, as shown in FIG. 2B, a control module 201, functional modules 202, and 203, of PCD 220a, may be executing a version of firmware included in a first version of a configuration package. As described above, a control module of a PCD 220 may include multiple memory banks, such as memory banks

205a, 205b. Similarly, as described above, a functional module 202, 203 may include multiple memory banks, such as memory bank 204a, 204b of functional module 202, and memory banks 206a, 206b of functional module 203. The first version of the configuration package may be stored in a memory bank 205a of a control module 201. A version of a firmware for a functional module 202 may be stored in a memory bank 204a, and a version of a firmware for a functional module 203 may be stored in a memory bank 206a, as shown in FIG. 2B.

As described above, a new configuration package comprising a new version of a firmware for one or more components of the PCD 220, such as control module 201, functional modules 202, 203, may be transmitted by server 102 to the PCD 220. The new versions of firmware may include respective instructions for adjusting a functional module based on a predefined parameter. For example, if functional module 202 includes a fluid pump module and the predefined parameter is a flow rate of the fluid pump module, then the new version of firmware for the functional module 202 may include instructions for controlling a flow rate of the functional module 202. Similarly, if functional module 203 includes a syringe pump module and the predefined parameter is a pressure applied to a syringe received by the syringe pump module, then the new version of firmware for the functional module 203 may include new or updated instructions for controlling pressure applied to the syringe pump module. The control module 201 may be configured to receive the new configuration package and store the received configuration package in a memory bank of the control module 201. The control module 201 may be configured to, on receiving the instructions, identify an available or free memory bank of the control module 201 to store the received configuration package. In the example shown in FIG. 2C, the control module 201 stores received configuration package in the available memory bank 205b. If the control module 201 determines that a memory bank is not available, then the control module 201 may be configured to determine the memory bank storing the oldest received firmware and store the received configuration package in the memory bank storing the oldest received firmware. The oldest received firmware may not be the oldest version of the firmware. A control module of a PCD 220, such as control module 201 of PCD 220a, may associate every received configuration package and/or firmware with a timestamp and store the timestamp along with the received configuration package. In some implementations, a timestamp may indicate a time at which the configuration package and/or firmware is received by the control module.

In response to receiving the new configuration package, the control module 201 may be configured to determine whether the new configuration package includes a new version of firmware for one or more components communicatively coupled and/or connected to the control module 201, such as functional module 202, 203. In some implementations, the control module 201 may receive information related to the different firmware included in a configuration package and the control module 201 may determine whether the configuration package includes a version of a firmware for a functional module communicatively coupled and/or connected to the control module 201 based on the information related to the different firmware included in the configuration package. For example, for the new configuration package stored in memory bank 205b, the control module 201 may receive information related that specifies that the new configuration package includes firmware ("L2") for functional modules that are large volume pump modules and firmware ("S2") for functional modules that are syringe modules, and based on such received information, the control module 201 determines that the received new configuration package includes firmware for functional module 203 (e.g., a large volume pump, as shown in FIG. 2C) and the functional module 202 (e.g., a syringe module, as shown in FIG. 2B).

In some implementations, a configuration package may be associated with a version number. For example, the configuration package stored in the memory bank 205a may be associated with a version number 1 and the new configuration package stored in the memory bank 205b may be associated with a version number 2. In some implementations, each firmware included in the configuration package may be associated with the version number of the configuration package. For example, firmware P1, L1, and, S1 included in the configuration package stored in memory bank 205a may be associated with version number 1 and firmware P2, L2, and S2 included in the configuration package stored in memory bank 205b may be associated with version number 2.

Figure 2D:
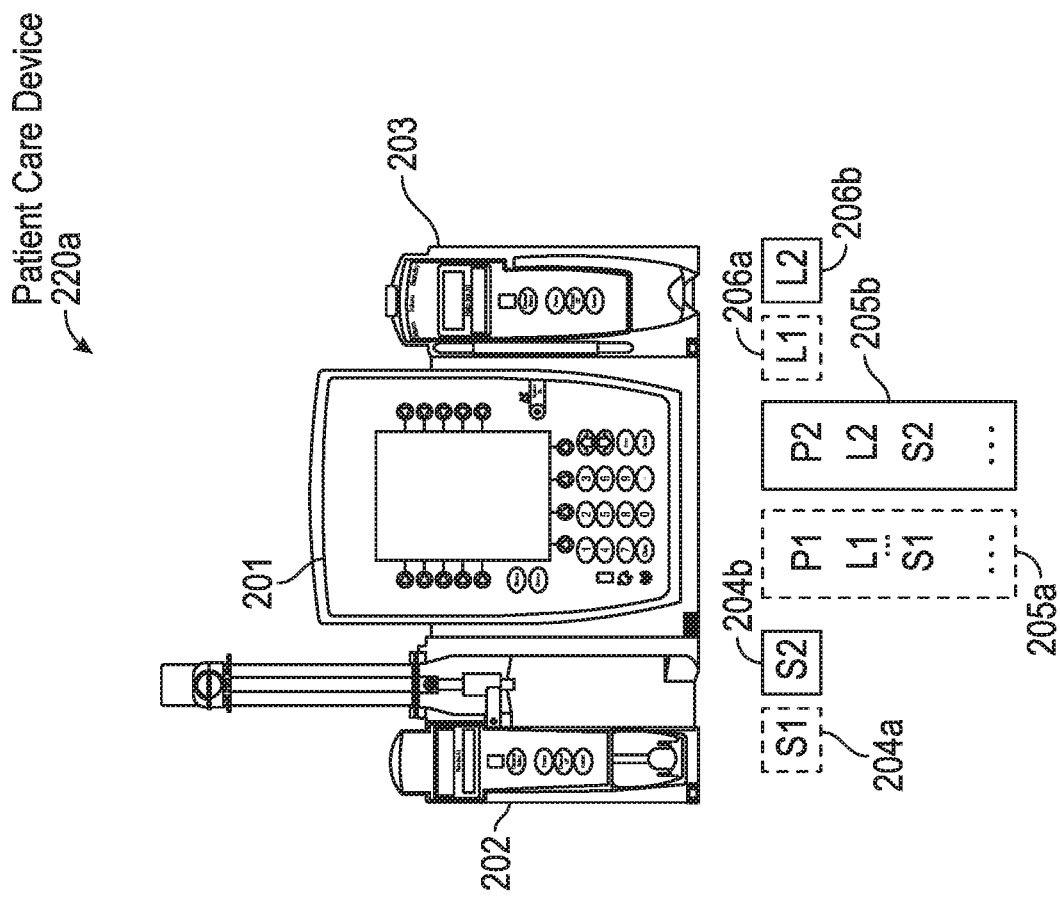

In some implementations, the control module 201 may transmit a message and/or an instruction, specifying a version of a firmware, to a functional module connected to the control module 201, such as the functional modules 202, 203, to determine whether the connected functional module includes the version of firmware. In some implementations, the functional module may transmit a message to the control module 201 indicating whether the functional module includes the specified version of firmware. Based on the received message from the functional module, the control module 201 determines whether the functional module includes the specified version of firmware. If the control module 201 determines that the functional module does not include the specified version of firmware, then the control module 201 may transmit the specified version of firmware to the functional module. For example, as shown in FIG. 2D, if the control module 201 determines that received configuration package includes a new version of firmware (e.g., "S2") for functional module 202 and the control module 201 determines that the functional module 202 does not include the new version of firmware S2, then the control module 201 transfers the firmware S2 to the functional module 202. Similarly, if the control module 201 determines that the received configuration package includes a new version of firmware (e.g., "L2") for the functional module 203 and that the functional module 203 does not include the new version of firmware L2, then the control module 201 transfers the firmware L2 to the functional module 203.

In some implementations, if a configuration package associated with the specified version of the firmware is not currently activated, then the control module 201 assigns a low priority to the transmission of specified version of firmware to the functional module and initiates the process of transmission of the specified version of firmware based on a priority of pending processes and available computing resources of the control module 201 (e.g., bandwidth of one or more processors and/or communication channels of the control module 201). Additional details of transmitting firmware based on available computing resources of the control module 201 and priority of the process are described herein with reference to FIGS. 3A-3C, and FIG. 8. In some implementations, if a configuration package associated with the specified version of the firmware is currently activated, then the control module 201 may immediately initiate the process of transmission of the specified version of firmware to the functional module and transmits an instruction to execute the specified version of firmware. Additional details of transmitting a version of firmware to functional modules and causing the functional module to execute the transmitted version of firmware are described herein with reference to FIGS. 5A-5C and 7A-7D.

A functional module, such as functional module 202, 203, may be configured to store received firmware in an available or free memory bank of the functional module, such as memory bank 204b, and 206b, respectively. For example, as shown in FIG. 2D, functional module 202 may store the received firmware in the available memory bank 204b, and functional module 203 may store the received firmware in the memory bank 206b. The functional module 202, 203, may be configured to associate a timestamp with the received firmware, and store the firmware along with the associated timestamp in a memory bank. Similar to the control module 201, if the functional modules 202, 203, determine that a memory bank is not available or free, then the functional module 202, 203 may determine a memory bank storing the oldest received firmware, and store the received firmware in that memory bank.

In response to detecting a connection from a new functional module, the control module 201 may be configured to determine whether the received configuration package includes firmware for the new functional module. An example of a control module detecting connection of a new functional module and transferring firmware to the new functional module is described herein with reference to FIGS. 3A-3C.

Figure 3A:
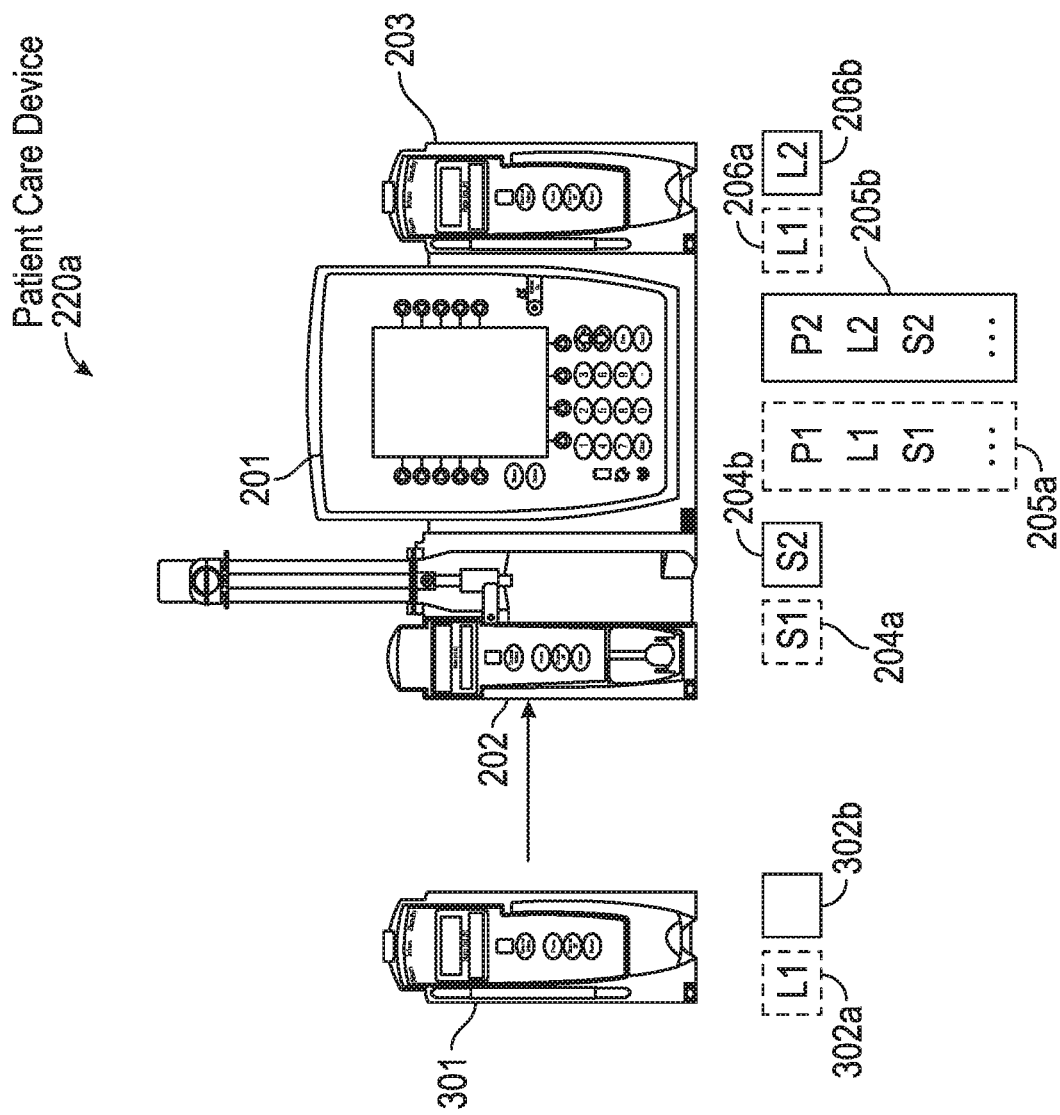

As shown in FIG. 3A, a new functional module 301 may be added to the PCD 220a by connecting the functional module 301 to a module and/or component of the PCD 220a. The functional module 301 may be electrically connected to control module 201. For example, as shown in FIG. 3B, the functional module 301 is electrically connected to the functional module 202. In some implementations, the new functional module, in response to a successful electrical connection with the PCD 220 may transmit a message to the control module of the PCD 220 indicating that the new functional module is successfully connected to the PCD 220. For example, in FIG. 3B, the functional module 301, in response to successfully establishing an electrical connection with the functional module 202, may transmit a message to the control module 201 indicating that the control module 301 is successfully connected to the PCD 220. In some implementations, the functional module that is directly physically and electrically connected to a new functional module, may transmit a message to the control module of the PCD 220 indicating that the new functional module is successfully connected. For example, in response to detecting a successful electrical connection from functional module 301, functional module 202 may transmit a message to the control module 201 indicating that the functional module 301 is successfully connected to the PCD 220a.

On a successful connection, the control module 201 may determine if a new version of firmware is available for the functional module 301, and transmit the new version of firmware to the functional module 301. The functional module 301 may be similarly configured as functional modules 202, 203, and may associate the received firmware with a timestamp, and store the received firmware along with an associated timestamp in a memory bank of the functional module 301 that is free and/or available, or storing the oldest received firmware. For example, as shown in FIG. 3C, the functional module 301 stores the received firmware in the available memory bank 302b. At this point, the received firmware is stored in the memory bank, but is not executed or activated.

As described above, a user of a terminal device 101, such as a biomedical technician, may transfer new configuration packages to PCD 220 that are currently in use in a medical facility, such as a hospital. The user may be presented with a user interface (e.g., a graphical user interface) on a display of terminal device 101 that displays information related to the new configuration packages transmitted to the PCD 220. The information displayed on the user interface includes, but is not limited to, a description of a version of configuration package transmitted to each PCD 220 in a configuration zone, a version of the PCD 220 in that configuration zone, a status of the transferred configuration package in the PCD 220 in a configuration zone, a number of PCD 220 in each configuration zone that have successfully received the configuration package, and the like. An example of such a user interface is the graphical user interface (GUI) shown in FIG. 4A. The GUI in FIG. 4A displays information related to the configuration packages transferred to the different configuration zones, along with information related to model numbers of a control module, and/or one or more functional modules of PCD 220. In some implementations, a user interface may display information related to a time at which the configuration packages were transferred to the PCD 220s. For example, as shown in FIG. 4, the GUI displays a date and time at which the configuration packages were transferred or deployed to PCD 220s associated with the various configuration zones.

The user interface may display information related to a percentage of PCD 220s in each configuration zone that received the recently transferred configuration package, as shown in the GUI in FIG. 4A. In some implementations, each PCD 220 may transfer a message back to the device management server 102 after the PCD 220 successfully receives and/or stores the configuration package in a memory bank of the PCD 220. In some implementations, each PCD 220 may transmit a message to the device management server 102 after a control module of the PCD 220 successfully transfers firmware to a functional module of the PCD 220.

The device management server 102 may be configured to determine a total number of PCD 220s that have successfully received and/or stored the configuration packages, and provide such information to a user in a user interface, as shown in the GUI in FIG. 4A. A user and/or an automated algorithm may use such information to determine whether to transfer an activation command to the PCD 220s. In some implementations, a device management server 102 may be configured to automatically transfer an activation command to PCD 220s when a predetermined threshold number of PCD 220s receive the transferred configuration package. For example, a predetermined threshold number of PCD 220s may be set to 80% of PCD 220s, and a device management server 102 may be configured to transfer an activation code when 80% of the PCD 220s receive or confirm receipt of a transferred configuration package. In some implementations, a device management sever 102 may be configured to determine, for a configuration zone, a number of PCD 220s that successfully received and/or stored the configuration package, and when the determined number of PCD 220s satisfy a predetermined threshold number of PCD 220s associated with that configuration zone, automatically transfer an activation command to the PCD 220s associated with that configuration zone. Similarly, a user may transfer an activation code when a predetermined threshold number of PCD 220*s* of a configuration zone successfully receives and/or stores the configuration package.

Figure 4B:
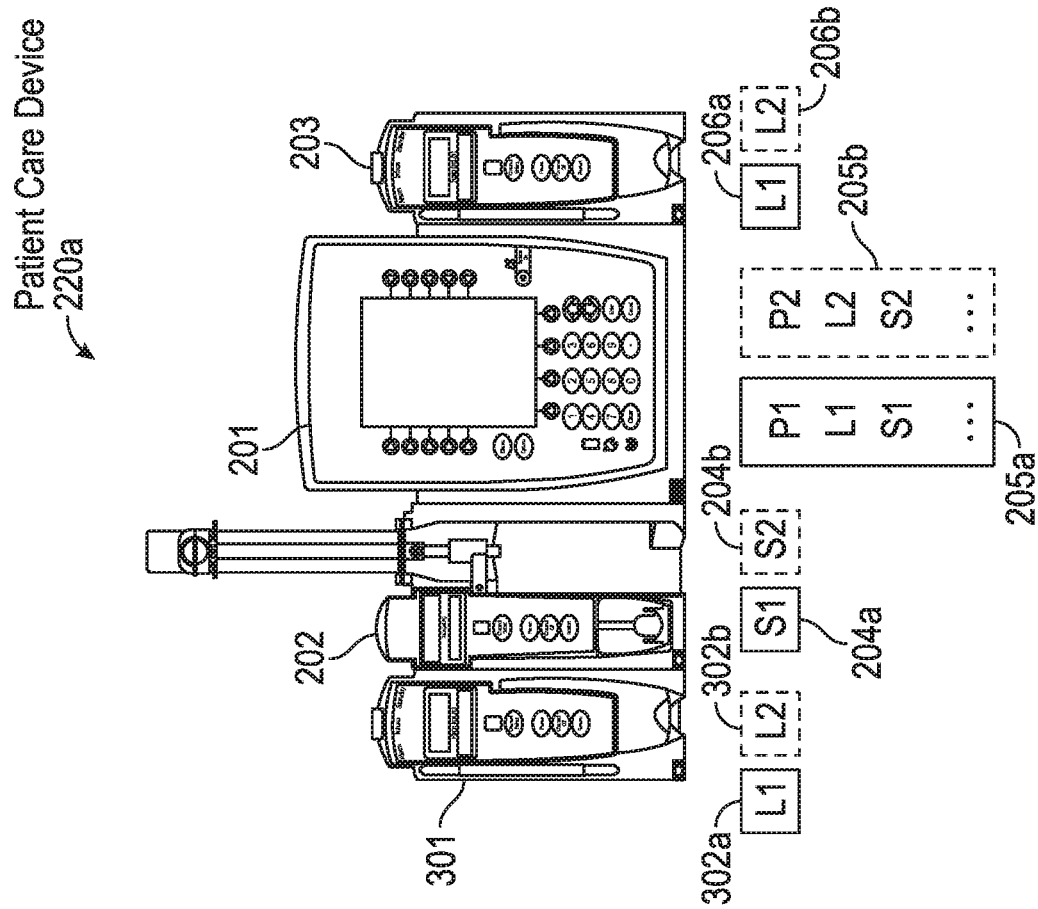

In response to receiving an activation code, a control module of a PCD 220 may be configured to switch to the execution of the most recently received firmware. The control module of the PCD 220 may be configured to switch to the execution of the most recently received firmware during a boot-up process of the PCD 220. In some implementations, the PCD 220 may be configured to automatically power down and boot-up if the PCD 220 is inactive and is not receiving interactions from a user and/or another system. For example, as described above, the control module 201 stores the received configuration package 108, and the included firmware for the control module 201 in memory bank 205*b*, as shown in FIG. 4B. Continuing with the example, during a boot-up after receiving the activation command, the control module 201 executes the firmware named "P2" stored in memory bank 205*b*.

In response to receiving an activation code, the control module 201 may be configured to transfer a command to one or more functional modules to execute their corresponding firmware. In some implementations, each functional module may be configured to power down and initiate a boot-up in response to the control module 201 powering down. Similar to the control module 201, the functional modules switch to the execution of the more recently received firmware during their boot-up process. Additional details of switching to recently received firmware is described herein with reference to FIGS. 8-10.

In some implementations, if a PCD 220 is connected with a new functional module that does not have a firmware compatible with and/or associated with the same configuration package with which the firmware executed on the control module of the PCD 220 is associated, then the control module of the PCD 220 may present an alert to a clinician providing an option to update the firmware of the functional module. An example of a PCD 220 providing an option to a user, such as a clinician, to update firmware of a newly connected functional module is shown in FIGS. 5A-5D.

Figure 5A:
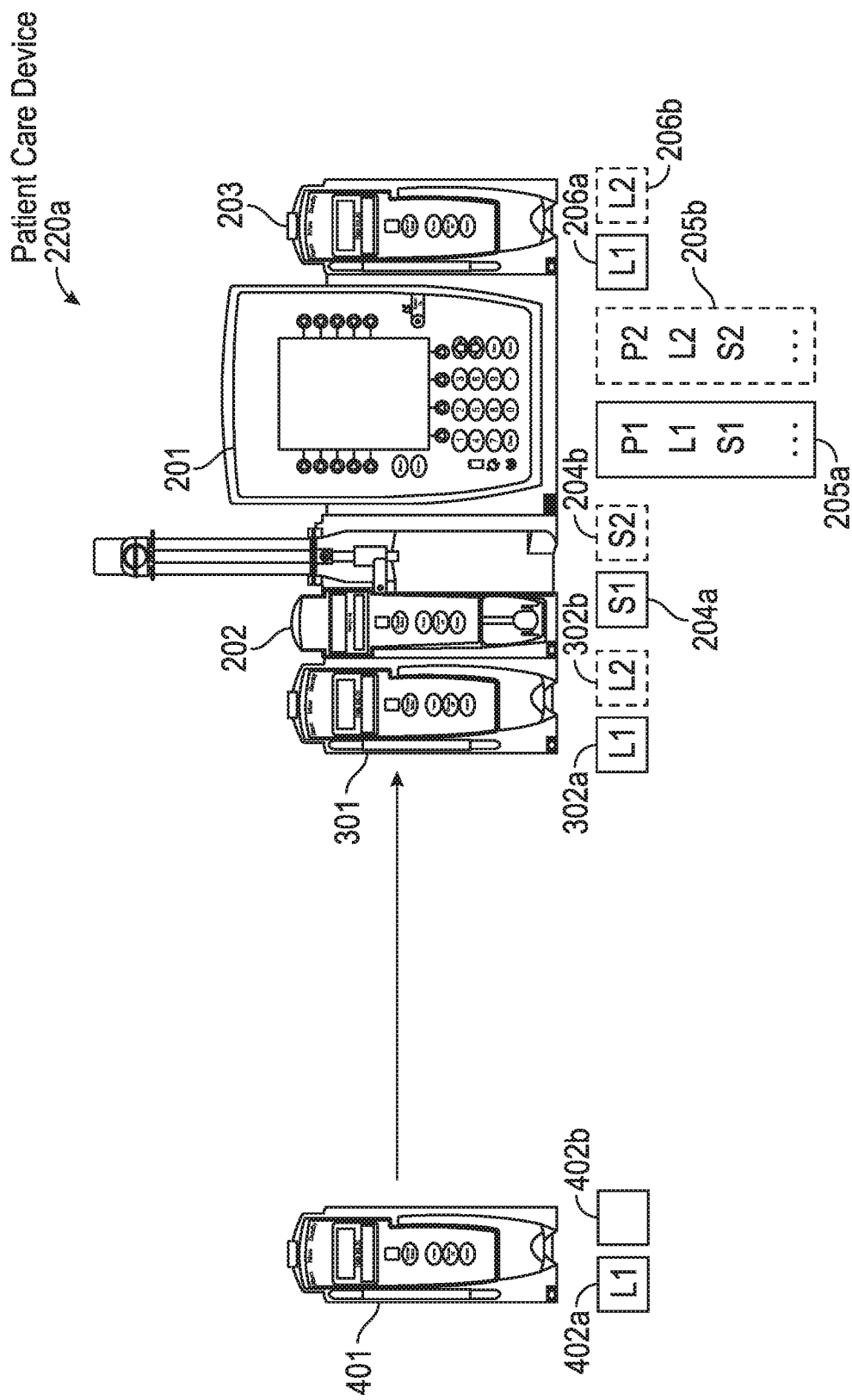
FIGS. 5A-FIG. 5D depict an example of transmission and execution of a version for firmware in a patient care device, according to illustrative implementations.
Figure 5B:
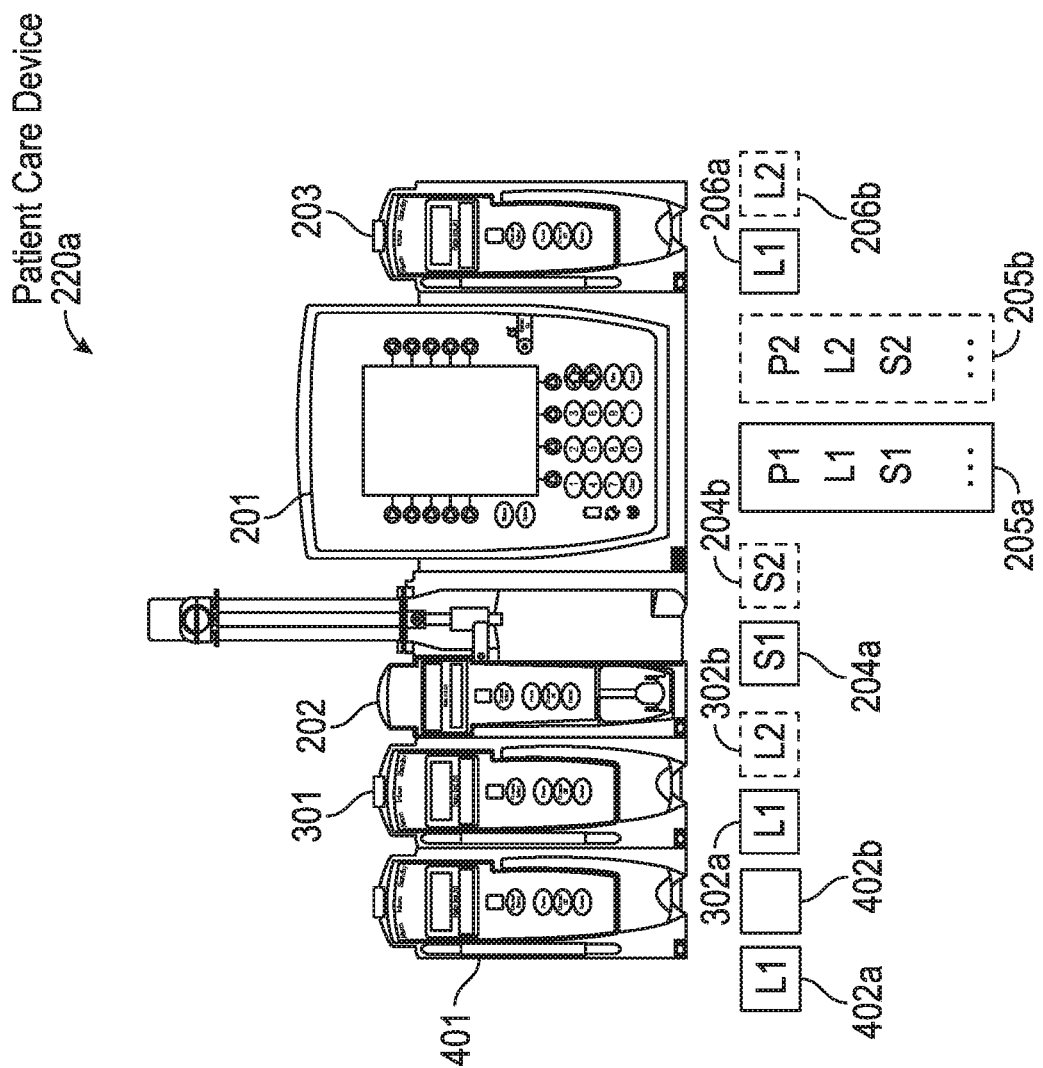

Turning now to FIGS. 5A-5D, there is shown an example of a new functional module 401 being connected with PCD 220*a*. The new functional module 401 may be similarly configured as functional modules 301, 202, 203. Continuing with the example depicted in FIG. 4B, control module 201 of the PCD 220*a* is executing firmware associated with the configuration package 108. As shown in FIG. 5A, the new functional module is not configured with firmware for functional module 401 that is associated with configuration package 108. The PCD 220 receives a connection from the functional module 401, as shown in FIG. 5B. The control module 201, in response to determining that the new functional module 401 does not have firmware compatible with and/or associated with the configuration package 108, may provide an alert to the user. The alert may display the amount of time the new functional module 401 will take to execute firmware compatible with and/or associated with the configuration package 108. The control module 201 may be configured to provide a user interface configured for receiving user inputs that provide instructions to the control module 201 to transfer a firmware for functional module 401 that is compatible with and/or associated with configuration package 108.

Figure 5C:
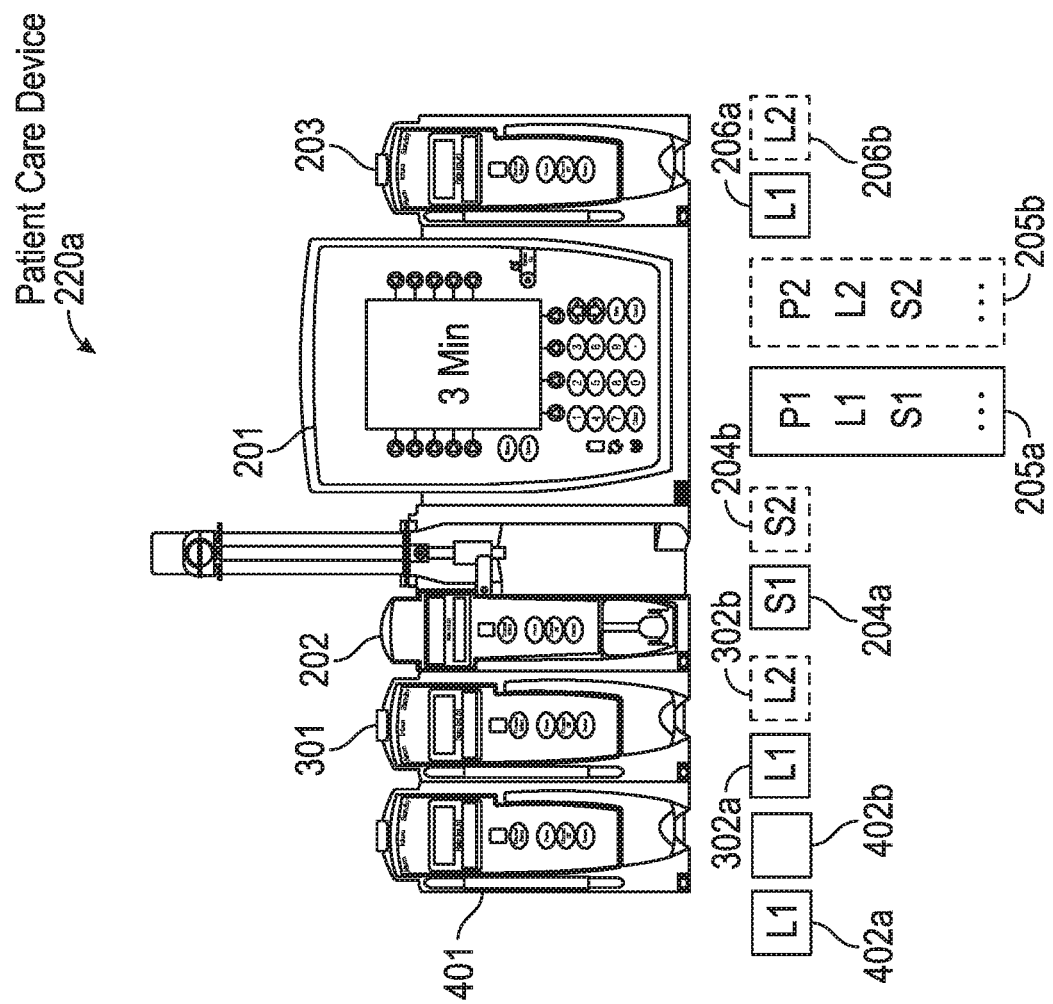
Figure 5D:
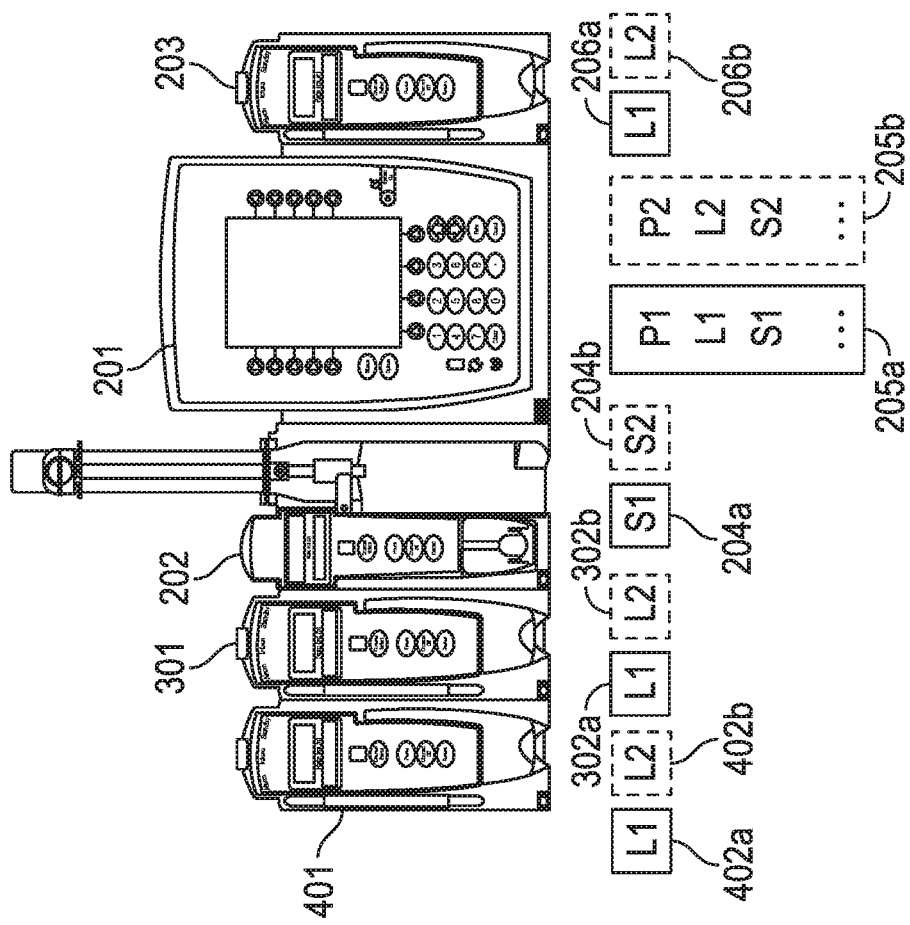

For example, as shown in FIG. 5C, the control module 201 presents a GUI alert that displays an amount of time that the functional module 401 may need to update to the firmware compatible with and/or associated with the compatible package 108. The GUI alert may include graphical items configured to receive inputs from the user that indicate whether the user is instructing the control module 201 to transmit the firmware compatible and/or associated with the firmware package 108 to the functional module 401. In response to receiving an input to transfer the firmware, the control module 201 may transfer the firmware to the functional module and cause the functional module 401 to power-down and boot-up to execute the transferred firmware. FIG. 5D illustrates the functional module 401 executing the firmware compatible and/or associated with the configuration package 108 after the power-down process.

A control module of a PCD 220 determines the version of firmware that each component, such as functional modules, of a PCD 220 will execute. A control module 220 may be configured to cause a newly connected functional module executing a more recent version of a firmware to execute an older version of a firmware that is compatible and/or associated with a configuration package with which the version of firmware that the control module is executing. Examples of a control module of a PCD 220 causing newly functional modules to execute older versions of firmware is shown in FIGS. 6A-7D.

Figure 6A:
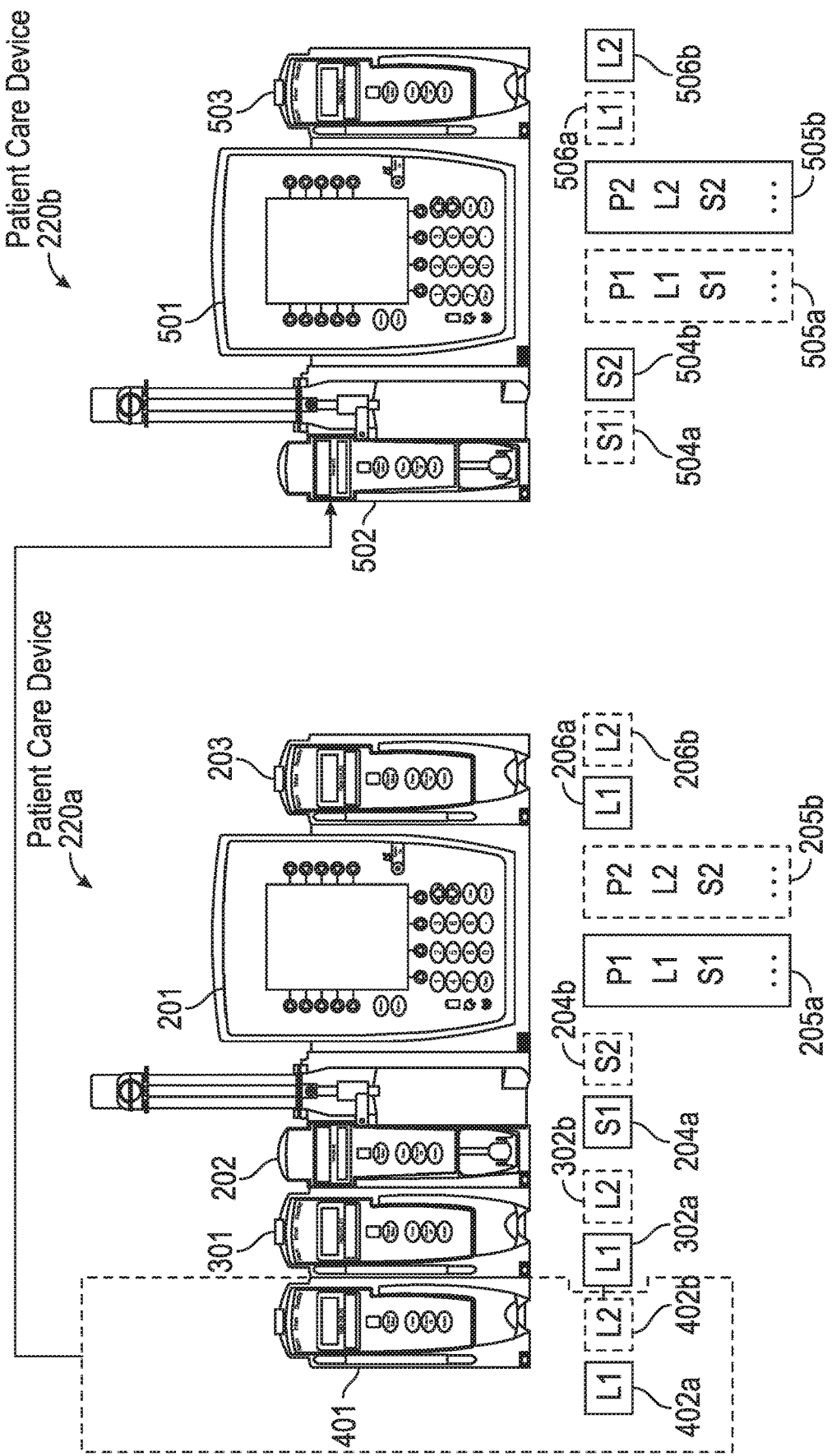
FIGS. 6A-FIG. 6C depict another example of transmission and execution of a version for firmware in a patient care device, according to illustrative implementations.

Turning now to FIG. 6A, the functional module 401 of PCD 220*a* is being connected to PCD 220*b*. As shown in FIG. 6A, components of PCD 220*b* (e.g., control module 501, functional modules 502, 503) have not yet activated firmware associated with the configuration package 108, whereas components of PCD 220*a* are executing firmware associated with configuration package 108. Control module 501 may be similarly configured as control module 201, and functional modules 502, 503 may be similarly configured as functional modules 202, 203.

Figure 6B:
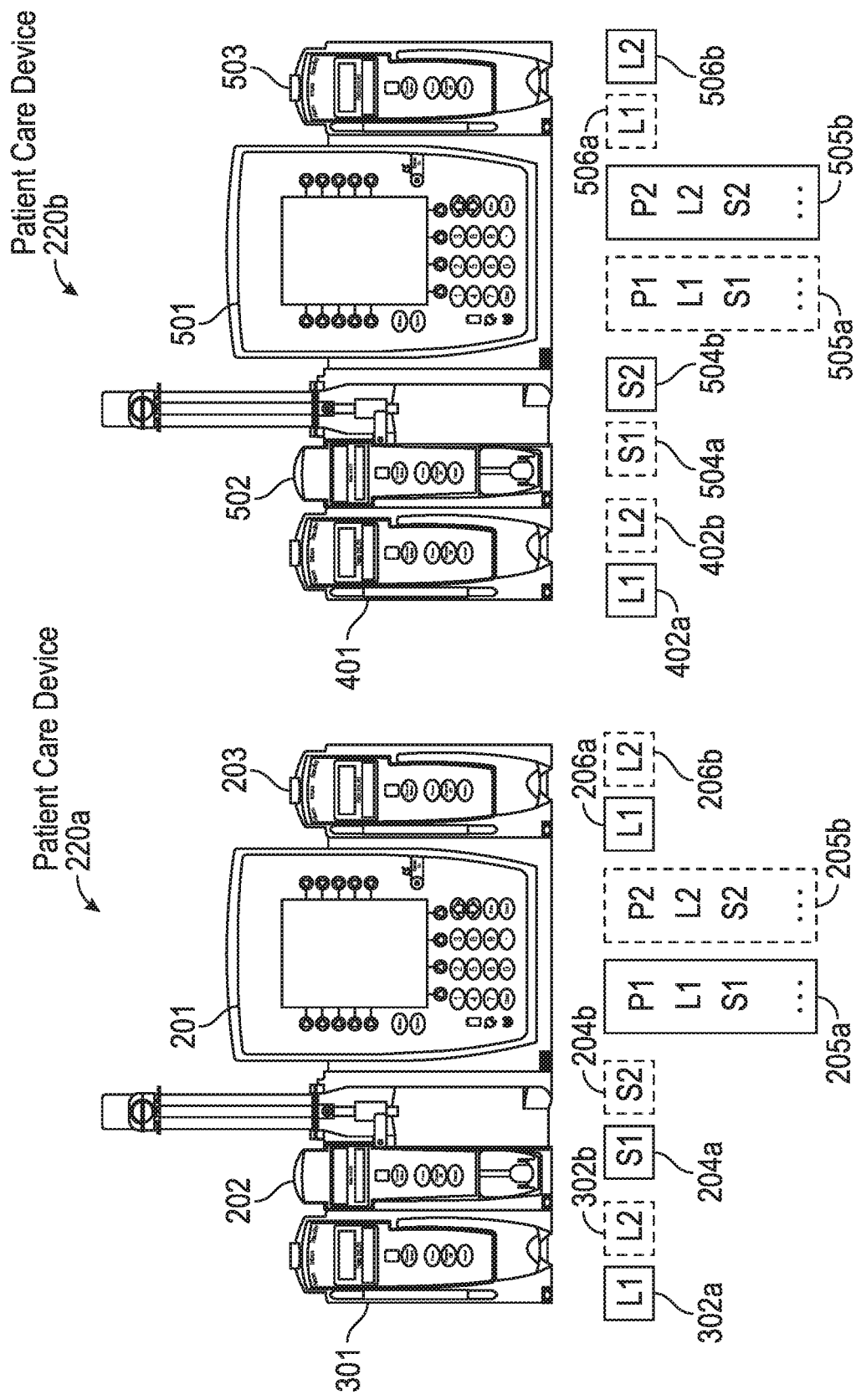
Figure 6C:
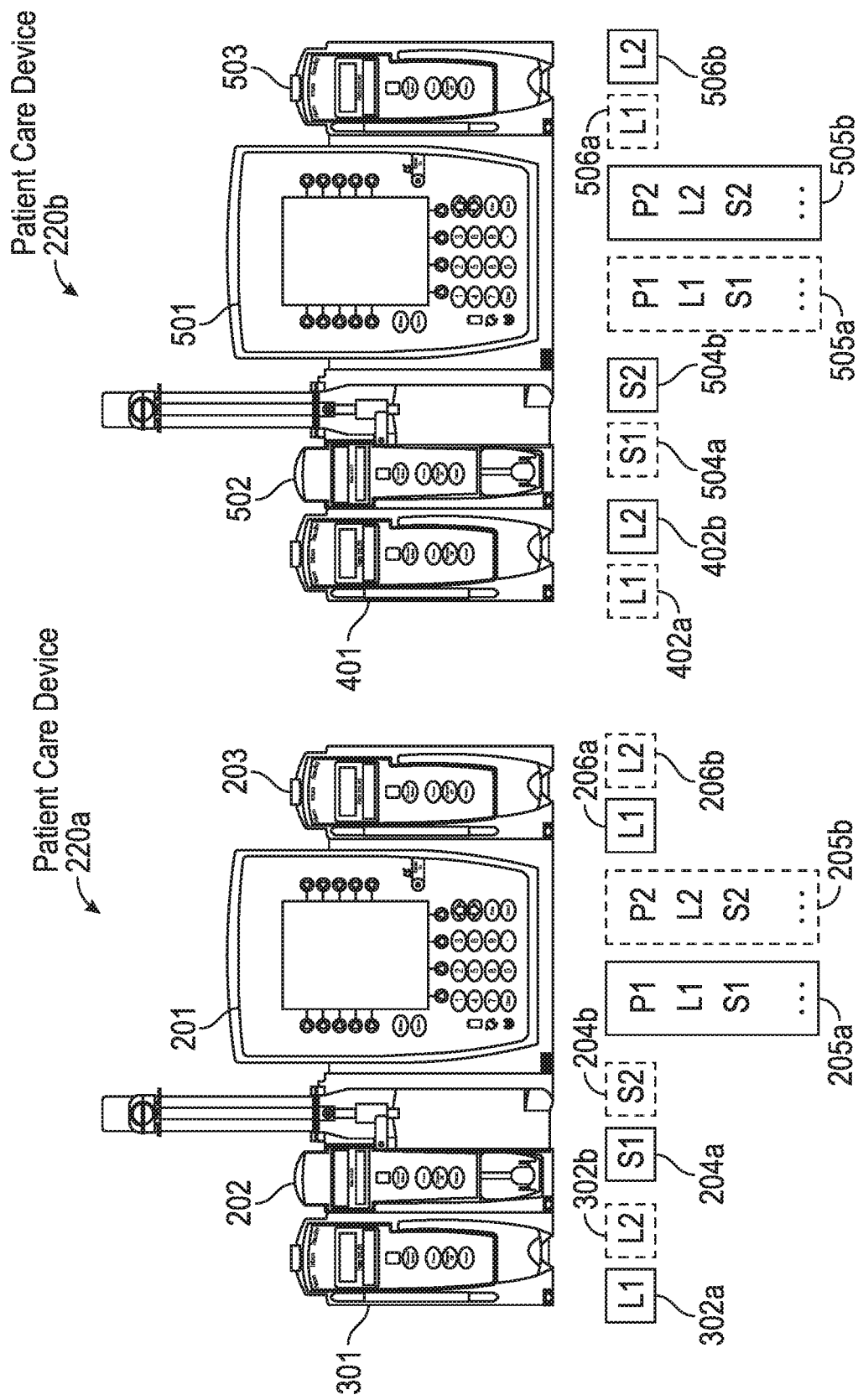

As shown in FIG. 6B, functional 401 is connected to PCD 220*b*. The control module 501, in response to detecting connection with functional module 401, may transfer an instruction to the functional module 401, to execute a version of firmware associated with a configuration package with which the firmware executing on the control module 501 is associated. In response to receiving the instruction to execute the version of firmware, the functional module 401 may be configured to determine whether the version of firmware is available, and execute that version of firmware if it is available. As described above, functional module 401 may be configured to execute a particular stored version of firmware different from the version of firmware it is currently executing by powering down, and switching to the particular stored version of firmware during a boot-up process. FIG. 6C illustrates the functional module 401 executing the firmware compatible and/or associated with the configuration package with which the firmware executed by the control module 501 is associated.

Figure 7A:
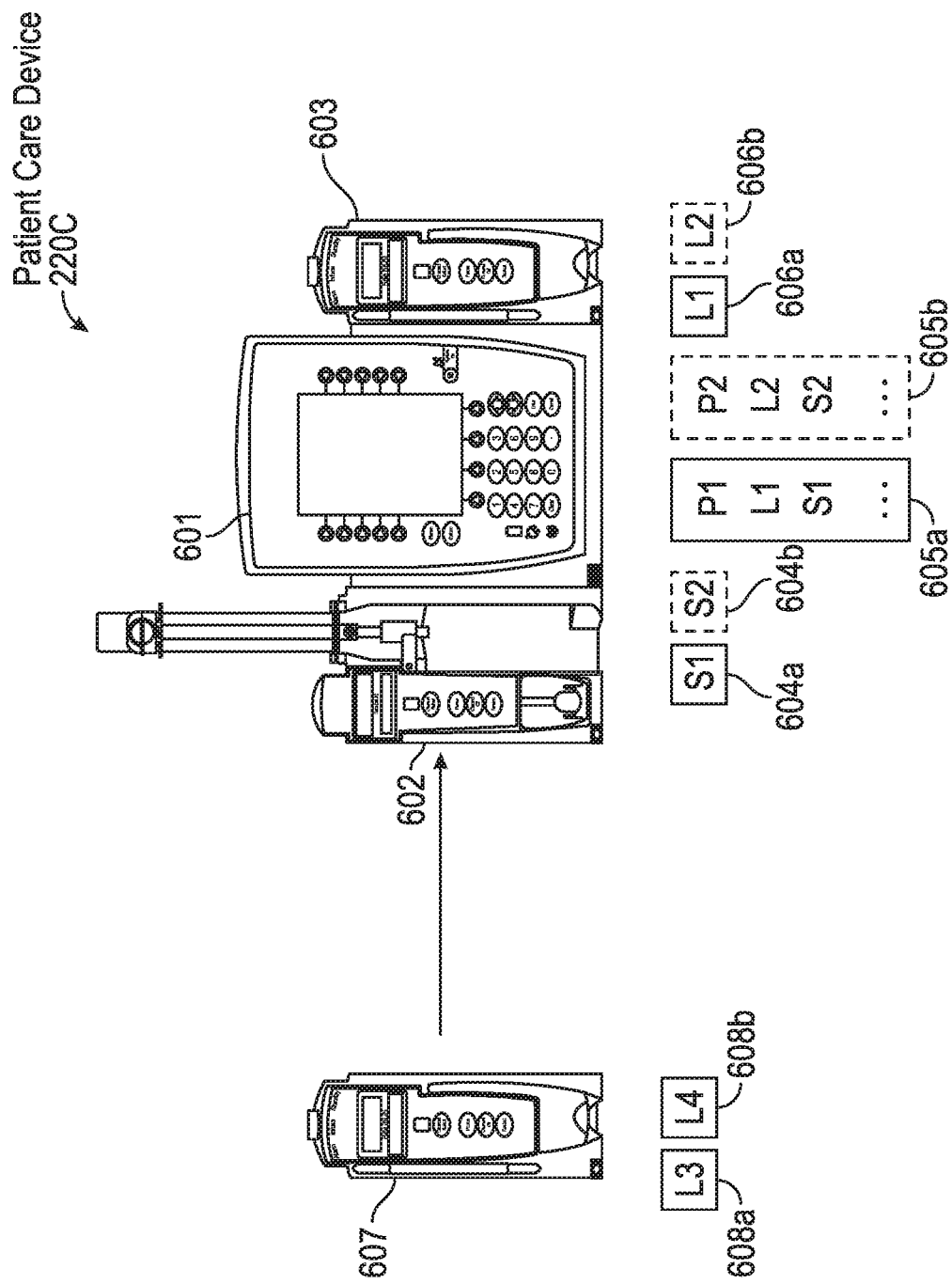
FIGS. 7A-FIG. 7D depict another example of transmission and execution of a version of firmware in patient care device, according to illustrative implementations.
Figure 7C:
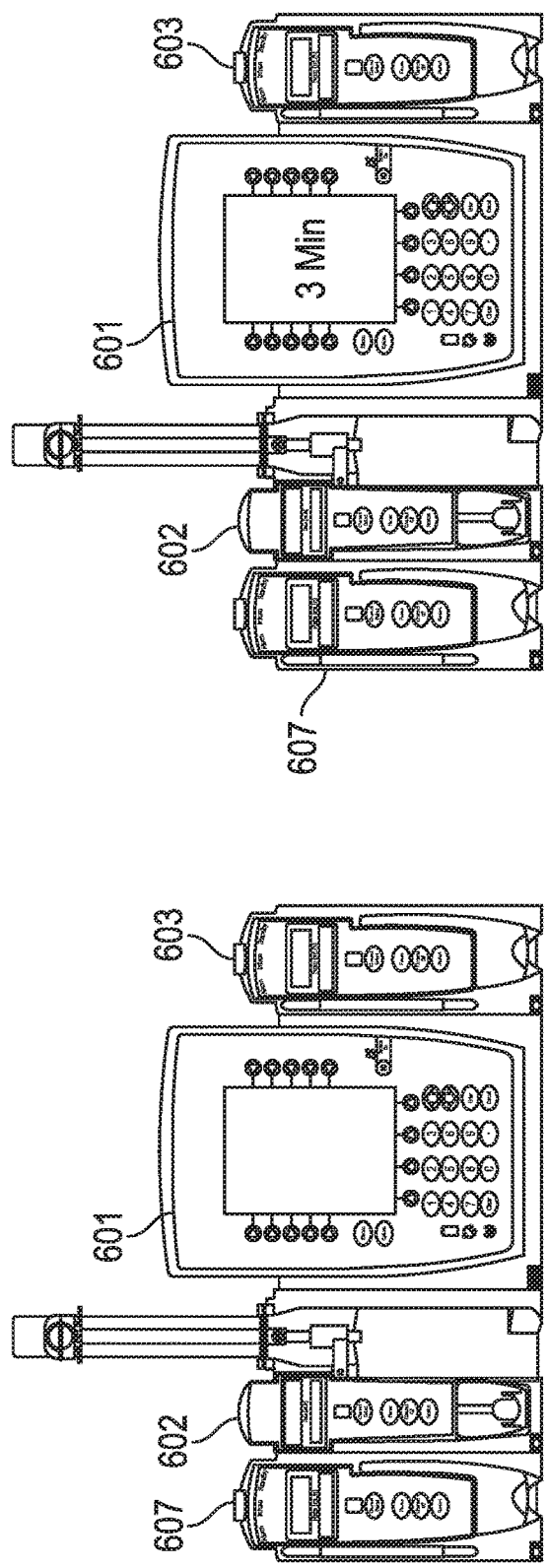

It is plausible that in some scenarios, a medical facility may rent functional modules from other medical facilities, and such the functional modules may be stored with versions of firmware that may be more up to date than the medical facility that is renting the functional modules. Example of such a functional module is shown in FIG. 7A. In FIG. 7A, there is shown a functional module 607 being connected to a PCD 220*c*. Control module 601 may be similarly configured as control modules 201 and 501, and functional modules 602, 603, 607 may be similarly configured as the functional modules described with reference to FIGS. 1A-6C, such as functional module 202, 203, 301, 401. As shown in FIG. 7A, the memory banks 608*a*, 608*b* of functional module 607 do not include combatible firmware and/or associated with the configuration package with which the firmware of the control module 601 is associated. The functional module 607 includes firmware that are later versions and not compatible and/or associated with the configuration packages stored in PCD 220c.

Figure 7B:
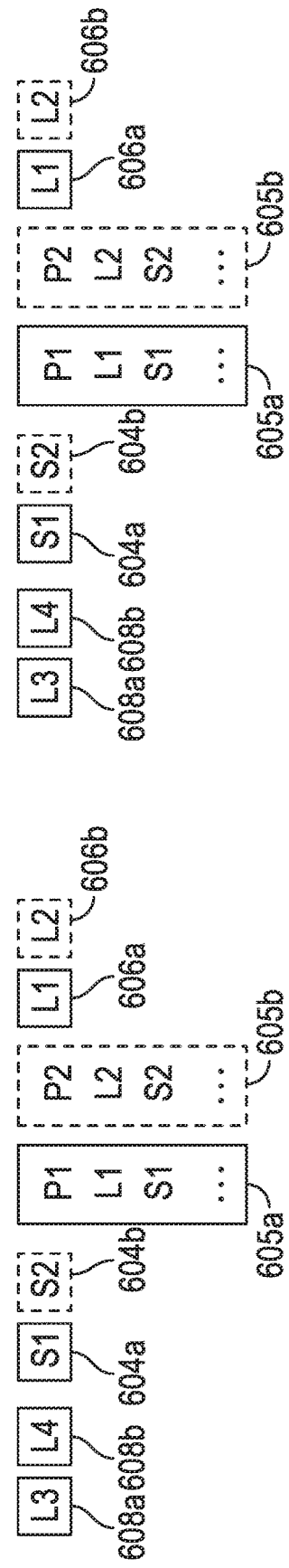
Figure 7D:
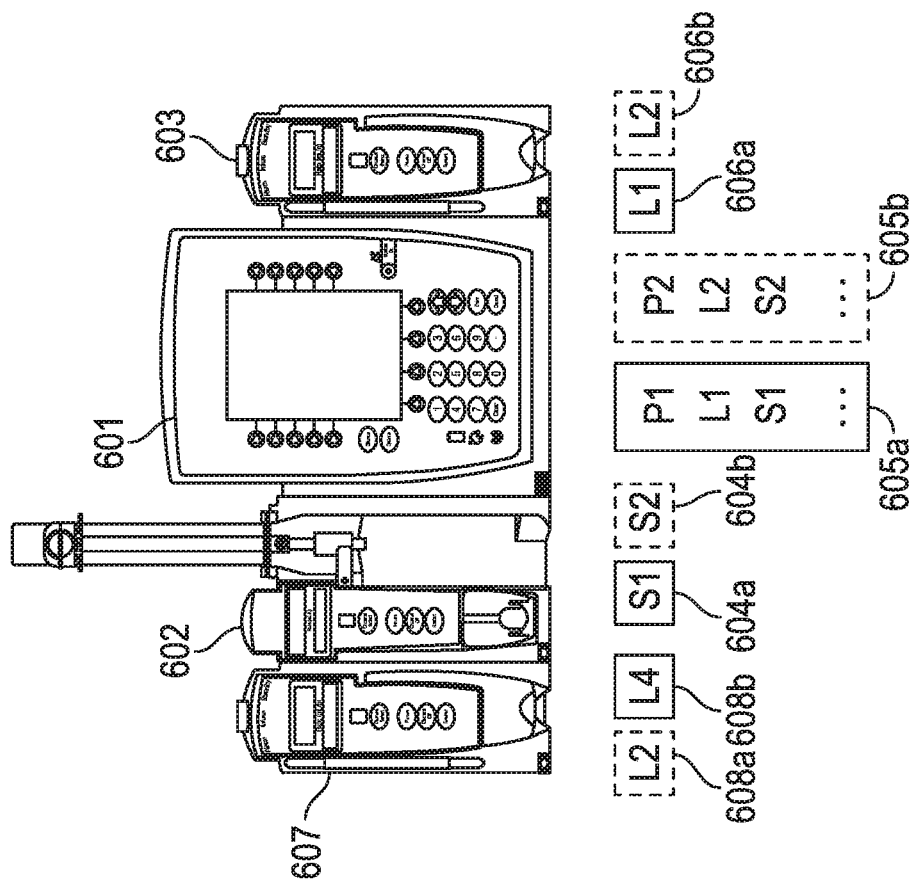

As shown in FIG. 7B, functional module 607 is connected to the PCD 220c. In response to the detection, the control module 601, similar to the control module 201 described above with reference to FIG. 5C, may transmit an instruction to functional module 607 to execute a version of firmware compatible and/or associated with the configuration package with which the firmware executed by the control module 601 is associated. Similar to control module 201, the control module 601, generates a presents a GUI alert that displays an amount of time that the functional module 607 may need to update to the firmware compatible and/or associated with the configuration package with which the firmware executed by the control module 601 is associated. In response to receiving an input to transfer the firmware, the control module 601 may transfer the firmware to the functional module 607 and cause the functional module 607 to execute the transferred firmware. Functional module 607 may be configured to switch execution of firmware similar to the techniques described herein with reference to FIGS. 1A-6C. FIG. 7D illustrates functional module 607 executing firmware compatible and/or associated with the configuration package with which the firmware executed by the control module 601 is associated. Additional details of transferring firmware and executing firmware are described herein with reference to FIGS. 8-10.

Figure 8:
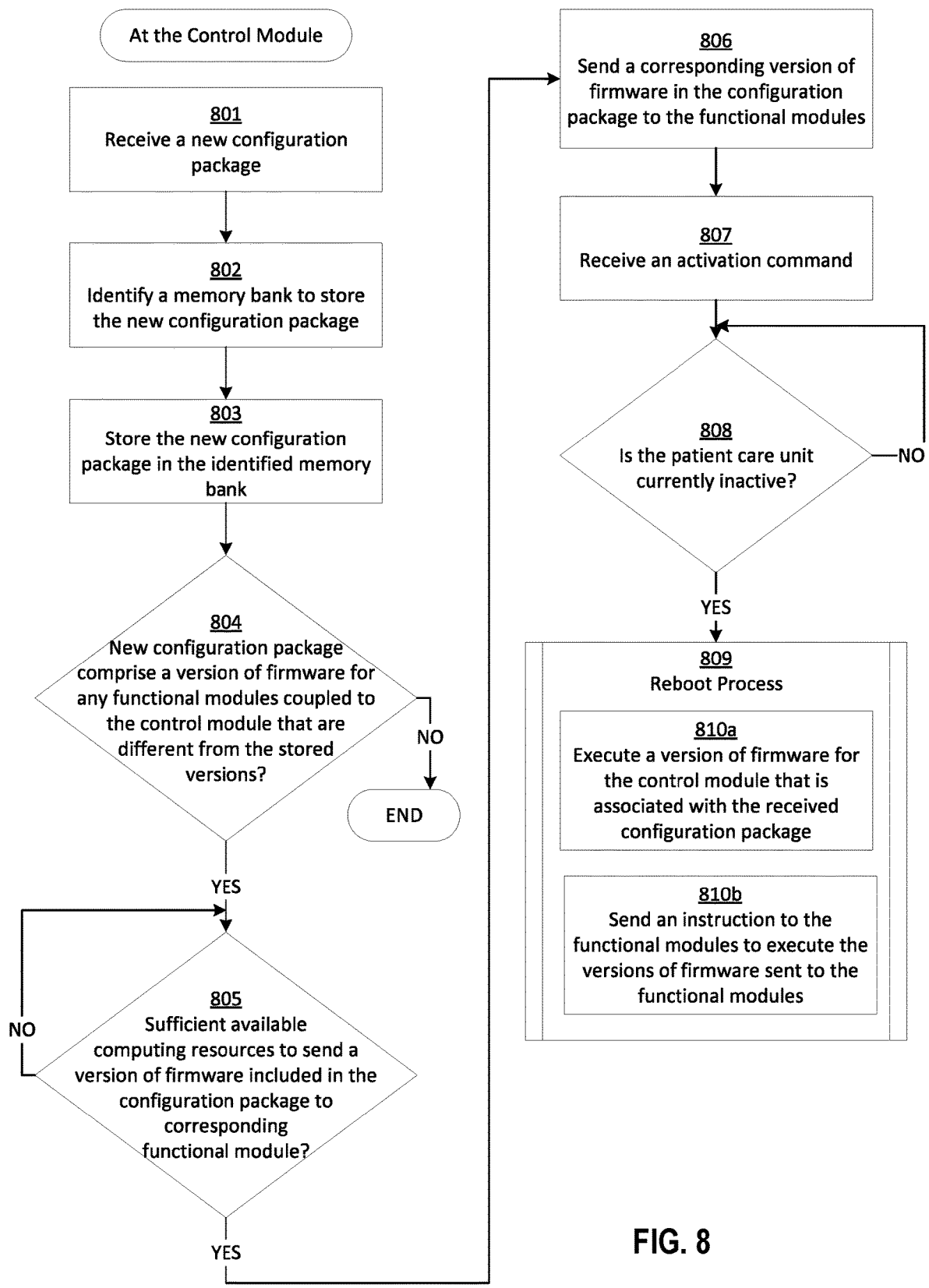
FIG. 8 is a flow chart of an example method of transmission and execution of firmware by a control module of a patient care device, according to illustrative implementations.

Turning now to FIG. 8, there is shown a flowchart illustrating a process of transferring and executing of firmware by a control module of a patient care device, such as control module 201 of the PCD 220a. For the purpose of illustrating a clear example, components of the patient care system 100 shown and described with reference to FIGS. 1A-7D are used to describe the process of transferring and executing the firmware.

The method 800 includes receiving, by a control module of a patient care device, a new configuration package (block 801). As described above, the configuration package may include firmware for one or more components of a patient care device 220, such as control module 201, functional modules 202 and 203 of PCD 220a. The firmware for one component of a PCD 220 included in the configuration package may be designed and/or tested to be compatible with firmware for the other components of the PCD 220 included in the configuration package.

The control module of PCD 220 identifies a memory bank to store the new configuration package (block 802). As described above, a control module (e.g., control module 201) of a PCD 220 may be configured to identify the memory bank that is free and/or available or the memory bank storing the oldest received configuration package. The control module of PCD 220 stores the new configuration package in the identified memory bank (block 803). According to some implementations, a second configuration package may be currently stored in a different, second memory bank of the control module when the new configuration package is received. In some implementations, the second configuration package may include a current version of firmware for at least one of the control module and the first functional module.

In the depicted example, the control module of the PCD 220 determines if the new configuration package includes a version of firmware for one or more functional modules coupled to the control module that are different from the stored versions of firmware (block 804). If the control module determines that the configuration package does not include versions of firmware for any functional modules coupled to the control module that are different than the stored versions ('NO' at block 804), then the method 800 proceeds to end of the method.

If the control module determines that the new configuration package includes a version of firmware for a functional module coupled to the control module that is different than the stored version ('YES' at block 804) (e.g., a new version), then the method 800 proceeds to block 805. The control module determines whether there are sufficient computing resources available to send a version of firmware included in the configuration package to the corresponding functional module (block 805). In some implementations, the control module may be configured to determine whether there are sufficient computing resources based on whether the amount of available processing power is below a certain threshold. For example, the control module may determine whether the amount of available processing power is below a certain threshold based on available bandwidth of one or more processors and/or communication channels of the control module. In some implementations, one or more processors of the control module may assign a low priority to the process of transferring the version of firmware to the functional module, and the one or more processors of the control module may be configured to initiate pending processes of the control module based on priorities assigned to the processes. In some implementations, the one or more processors of the control module may initiate a low priority process if available bandwidth of the one or more processors and/or communication channels of the control module satisfies a threshold bandwidth level. If the control module determines that sufficient computing resources are not available to send a version of firmware in the configuration package ('NO' at block 805), then the method 800 proceeds back to block 805 to wait for sufficient computing resources to become available.

If the control module determines that sufficient computing resources are available ('YES' at block 805), then the method 800 proceeds to block 806. The control module sends (e.g., transmits) a corresponding version of firmware in the configuration package to the functional modules (block 806). For example, if the functional modules connected to a control module of a PCD 220 are a pump and a physiological monitor, then the control module may send the firmware for a pump included in the received configuration package to the pump, and sends a firmware for the physiological monitor in the received configuration package to the physiological monitor. The transmitted version may be stored on the pump in a different memory bank than a memory bank currently storing a firmware currently used by the pump.

The control module receives an activation command (block 807). In some implementations, the control module may store an indication of receiving the activation command in a storage unit of the control module. For example, the control module may set a bit or store a value in a storage unit that indicates that the control module received the activation command. In response to receiving the activation command, the control module determines whether the PCD 220 is currently inactive (block 808). If the control module determines that the PCD 220 is currently active ('NO' at block 808), then the method 800 proceeds back to the block 808. The control module may be configured to wait until the PCD 220 is inactive prior to executing the version of firmware included in the received configuration package.

If the control module determines that the PCD 220 is currently inactive ('YES' at block 808), then the method 800 proceeds to block 809. The control module initiates a reboot process (block 809). As described above, a control module of a PCD 220 may initiate a reboot process by powering itself off and powering itself on. During the reboot process, the control module executes a version of firmware for the control module included in the received configuration package (block 810a). As described above, the control module switches to the version of firmware included in the configuration package by executing the firmware for a control module of a PCD 220 included in the received configuration package. During the reboot process, the control module sends an instruction to the functional modules to execute the versions of firmware sent to the functional modules (block 810b).

In some implementations, the control module of a PCD 220 may be configured to track a period of time that has elapsed since switching execution to a more recently received version of a firmware. In such implementations, if the period of time satisfies a threshold period of time, then the control module may be configured to delete the earlier received version of firmware from which execution was switched to a more recently received version of firmware. For example, a threshold period of time may be specified as five years, and if the tracked period of time since switching execution from a first version of firmware to another version of firmware equals five years, then the control module may delete that first version from the memory bank in the control module in which it is stored. In some implementations, the control module may receive a delete command from a user and/or a central system, such as the device management server 102, and the control module may be configured to delete the oldest received version of firmware from its memory banks. In some implementations, deletion of an oldest received version of firmware may optimize the process of storing of a more recently received firmware since the memory bank storing the oldest received version may be free and/or readily available to receive new firmware without incurring resource overhead (e.g., processing, power, memory, etc.) associated with data movement operations. In some implementations, the functional modules described herein may be configured to similarly delete older received versions of firmware.

As described above, the versions of firmware sent to the functional modules are included in the configuration package. As described above, the control module may cause the functional modules to restart themselves by sending an instruction to execute the versions of firmware sent by the control module to the functional modules. Additional details of a functional module of a PCD 220 executing a version of firmware received from a control module of a PCD 220 is described herein with reference to FIG. 9.

Figure 9:
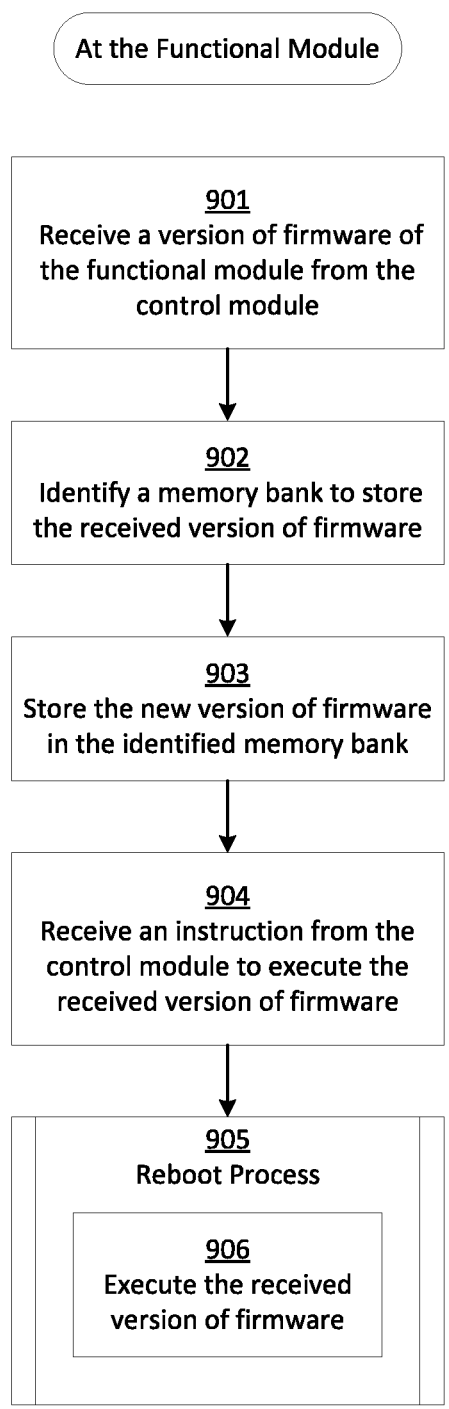
FIG. 9 is a flow chart of an example method of receiving and executing firmware by a functional module of a patient care device, according to illustrative implementations.

Turning now to FIG. 9, there is shown a flowchart illustrating a process of receiving and executing a firmware. For the purpose of illustrating a clear example, components of the patient care system 100 shown and described with reference to FIGS. 1A-7D are used to describe the process of transferring and executing the firmware.

The method 900 includes receiving, by a functional module of a patient care device 220, a version of firmware for the functional module from the control module (block 901). As described above, the version of firmware received by the functional module is included in the new configuration package received by the control module. The functional module of the patient care device 220 identifies a memory bank to store the received version of firmware (block 902).

As described above, a functional module of the patient care device 220 may be configured with multiple banks of memory, and the functional module may be configured to store the received version of firmware in a free and/or available memory bank or a memory bank storing the oldest received firmware. The functional module of the patient care device 220 stores the received version of firmware in the identified memory bank (block 903). In some implementations, the functional module of the PCD 220 may be configured to transmit a message to the control module of the PCD 220 that the received version of firmware is successfully stored in the functional module of the PCD 220.

The functional module of the PCD 220 receives an instruction from the control module to execute the received version of firmware (block 904). The functional module of PCD 220 initiates a reboot process (block 905). As described above, the functional module of PCD 220 may be configured to initiate a reboot process in response to receiving an instruction from the control module to execute the received version of firmware. The functional module, similar to the control module, may be configured to store an indication of receiving the instruction from the control module to execute the received version of firmware. For example, the functional module may set a bit and/or store a value in a storage unit that indicates that the functional module received an instruction from the control module to execute the received version of firmware. During the reboot process, the functional module executes the received version of firmware (block 906). The functional module, during the boot-up process of the reboot process, may be configured to determine whether the functional module received an instruction to execute the received version of firmware from the control module. For example, the functional module may check the storage unit to determine whether the stored value or bit indicates that an instruction to execute the received version of firmware is received from the control module. If the stored value or bit indicates that the instruction is received, then the functional module executes the received version of firmware during the boot-up process of the reboot process.

Figure 10:
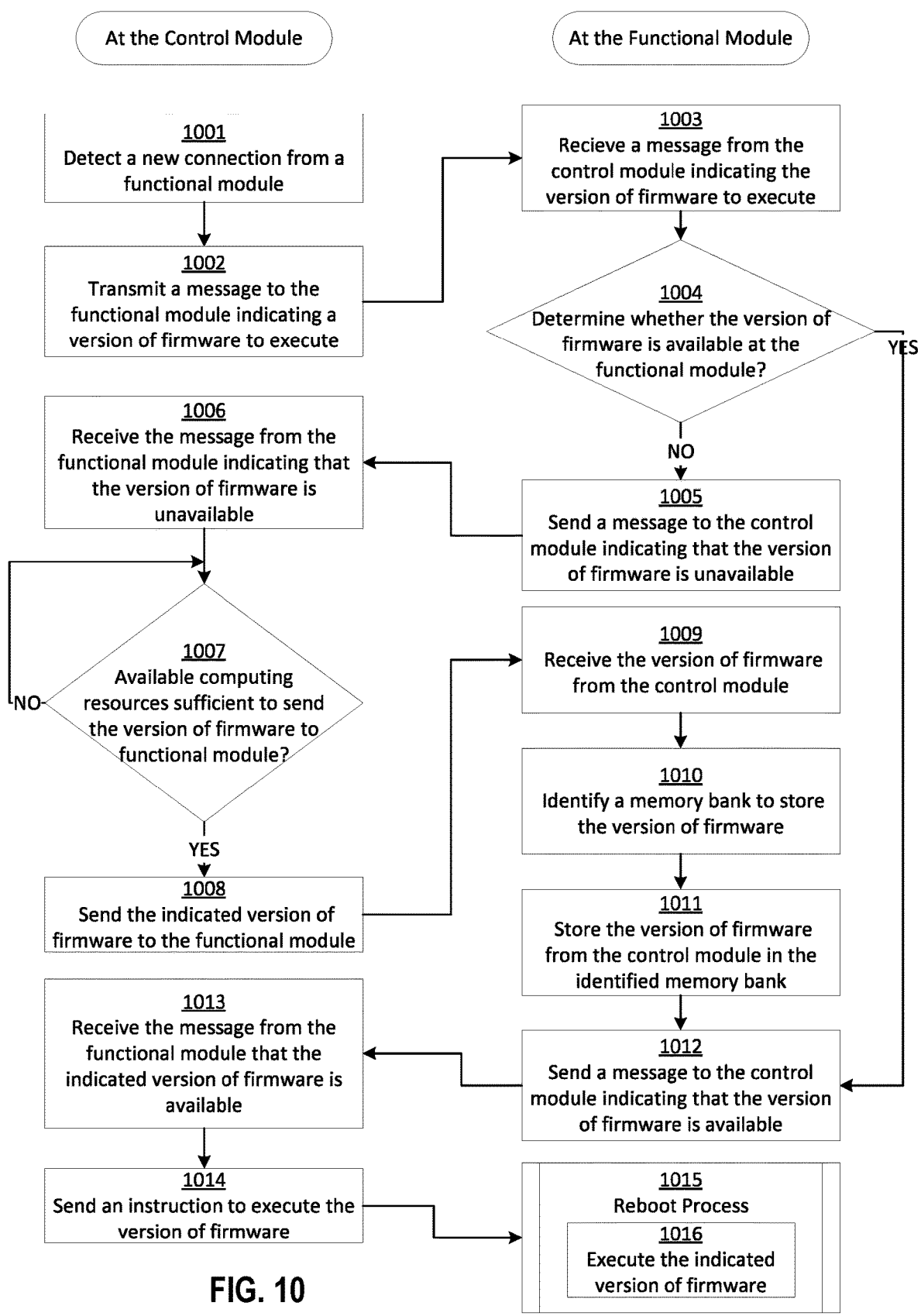
FIG. 10 is a flow chart of an example method of detecting connection of a functional module by a control module and sending firmware by the control module, according to illustrative implementations.

Turning now to FIG. 10, there is shown a flowchart illustrating another process of sending firmware to a functional module of a patient care device and causing execution of the firmware by the control module of the patient care device. For the purpose of illustrating a clear example, components of the patient care system 100 shown and described with reference to FIGS. 1A-7D are used to describe the process of transferring and executing the firmware.

The method 1000 includes detecting, by a control module of PCD 220, a new connection from a new functional module (block 1001). As described above, the control module may be configured to detect electrical connection one or more modules of a PCD 220. The control module may transmit a message to the functional module indicating a version of firmware to execute (block 1002). For example, in response to detecting a new connection from a functional module, the control module of the PCD 220 transmits a message to the functional module that specifies a version of firmware to execute. The method 1000 proceeds to the block 1003.

The functional module receives the message from the control module that indicates the version of firmware to execute (block 1003). The functional module determines whether it has the version of firmware indicated in the message (block 1004). If the functional module determines that the version of firmware is available ('YES' at block 1004), then the method 1000 proceeds to block 1012.

Additional details of block 1012 are provided below. If the functional module determines that the version of firmware is not available ('NO' at block 1004), then the method proceeds to block 1005. The functional module sends a message to the control module indicating that the version of firmware is unavailable (block 1005). The method proceeds to the block 1006.

The control module receives the message from the functional module that the indicated version of firmware that the version of firmware is unavailable (block 1006). The control module determines whether the available computing resources of the PCD 220 are sufficient to send the indicated version of firmware to the functional module. If the control module determines that the available computing resources are not sufficient ('NO' at block 1007), then the method 1000 proceeds back to block 1007. If the control module determines that the available computing resources are sufficient ('YES' at block 1007), then the method 1000 proceeds to the block 1008

The control module of the PCD 220 sends the indicated version of firmware to the functional module (block 1008). The functional module of the PCD 220 receives the indicated version of firmware from the control module (block 1009). The functional module of the PCD 220 identifies a memory bank to store the received version of firmware (block 1010), and stores the received version of firmware in the identified memory bank (block 1011). Additional details of identifying memory banks and storing firmware in the identified memory banks are described above. The functional module sends a message to the control module indicating that the indicated version of the firmware is available (block 1012). The message proceeds to block 1013.

The control module of the PCD 220 receives the message from the functional module that the indicated version of firmware is available (block 1013). The control module sends an instruction to execute the indicated version of firmware (block 1014). The method proceeds to block 1015. The functional module initiates the reboot process (block 1015), and, during the reboot process, the functional module executes the indicated version of firmware (block 1016). Additional details of the functional module indicating the reboot process and the executing a version of firmware during the reboot process are described with reference to the previously described figures.

Many of the above-described examples, and related features and applications, may also be implemented as software processes that are specified as a set of instructions recorded on a computer readable storage medium (also referred to as computer readable medium), and may be executed automatically (e.g., without user intervention). When these instructions are executed by one or more processing unit(s) (e.g., one or more processors, cores of processors, or other processing units), they cause the processing unit(s) to perform the actions indicated in the instructions. Examples of computer readable media include, but are not limited to, CD-ROMs, flash drives, RAM chips, hard drives, EPROMs, etc. The computer readable media does not include carrier waves and electronic signals passing wirelessly or over wired connections.

The term "software" is meant to include, where appropriate, firmware residing in read-only memory or applications stored in magnetic storage, which can be read into memory for processing by a processor. Also, in some implementations, multiple software aspects of the subject disclosure can be implemented as sub-parts of a larger program while remaining distinct software aspects of the subject disclosure. In some implementations, multiple software aspects can also be implemented as separate programs. Finally, combinations of separate programs that together implement a software aspect described here is within the scope of the subject disclosure. In some implementations, the software programs, when installed to operate on one or more electronic systems, define one or more specific machine implementations that execute and perform the operations of the software programs.

A computer program (also known as a program, software, software application, script, or code) can be written in a programming language, including compiled or interpreted languages, declarative or procedural languages, and it can be deployed in a machine-executable form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Figure 11:
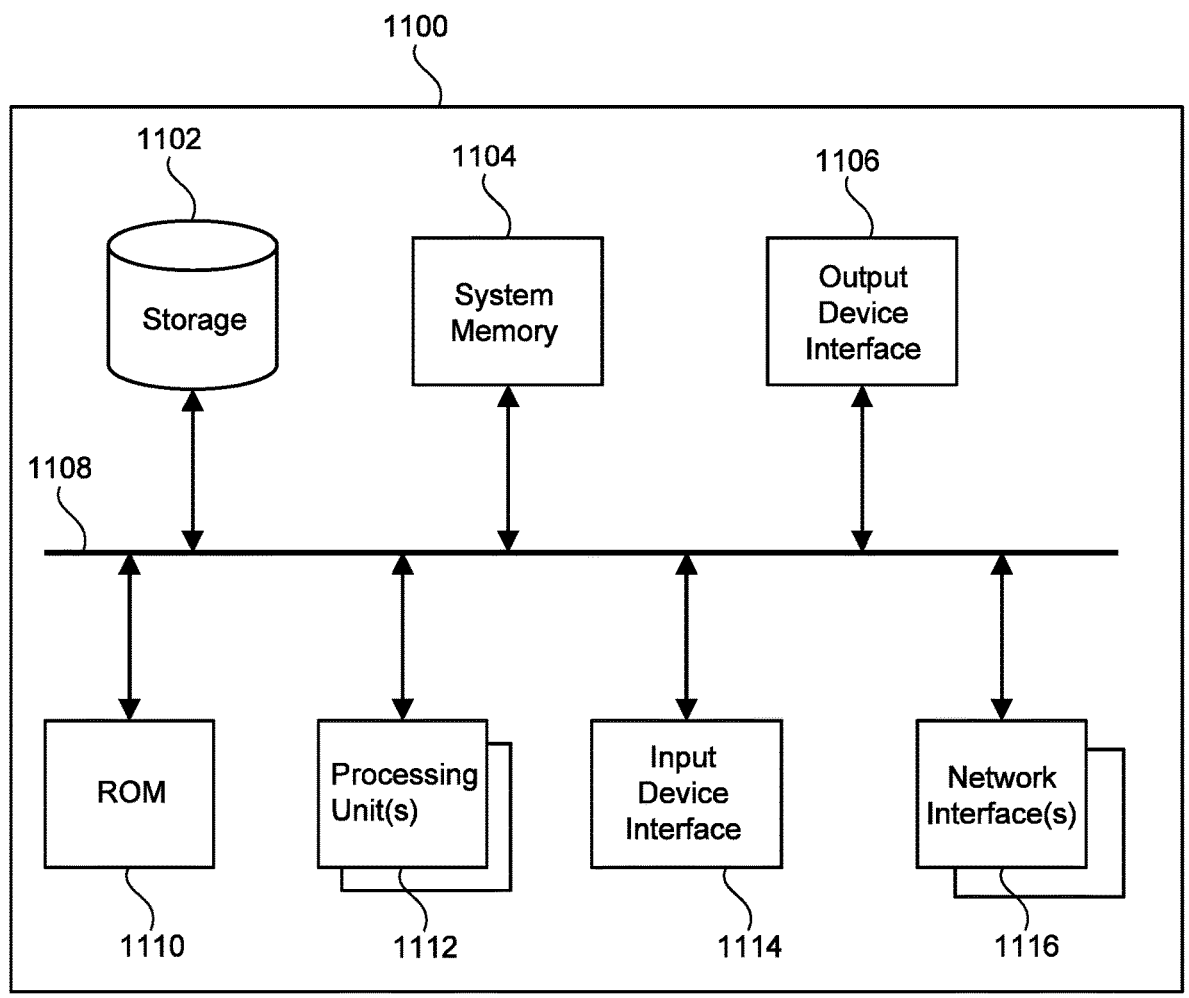
FIG. 11 is a conceptual diagram illustrating an example electronic system 1100 for the automatic provisioning of medical devices, according to aspects of the subject technology.

FIG. 11 is a conceptual diagram illustrating an example electronic system 1100 for the optimized process of updating firmware across medical devices while minimizing clinical impact, according to aspects of the subject technology. Electronic system 1100 may be a computing device for execution of software associated with one or more portions or steps of process 400, or components and processes provided by FIGS. 1A-10, including but not limited to device management server 102, computing hardware within patient care devices 220, or terminal device 101. Electronic system 1100 may be representative, in combination with the disclosure regarding FIGS. 1A-10. In this regard, electronic system 1100 may be a personal computer or a mobile device such as a smartphone, tablet computer, laptop, PDA, an augmented reality device, a wearable such as a watch or band or glasses, or combination thereof, or other touch screen or television with one or more processors embedded therein or coupled thereto, or other sort of computer-related electronic device having network connectivity and specifically configured to implement one or more of the features described.

Electronic system 1100 may include various types of computer readable media and interfaces for various other types of computer readable media. In the depicted example, electronic system 1100 includes a bus 1108, processing unit(s) 1112, a system memory 1104, a read-only memory (ROM) 1110, a permanent storage device 1102, an input device interface 1114, an output device interface 1106, and one or more network interfaces 1116. In some implementations, electronic system 1100 may include or be integrated with other computing devices or circuitry for operation of the various components and processes previously described.

Bus 1108 includes one or more of: system, peripheral, and chipset buses that communicatively connect the numerous internal devices of electronic system 1100. For instance, bus 1108 communicatively connects processing unit(s) 1112 with ROM 1110, system memory 1104, and permanent storage device 1102.

From these various memory units, processing unit(s) 1112 retrieves instructions to execute and data to process in order to execute the processes of the subject disclosure. The processing unit(s) can be a single processor or a multi-core processor in different implementations.

ROM 1110 stores static data and instructions that are needed by processing unit(s) 1112 and other modules of the electronic system. Permanent storage device 1102, on the other hand, is a read-and-write memory device. This device is a non-volatile memory unit that stores instructions and data even when electronic system 1100 is off. Some implementations of the subject disclosure use a mass-storage device (such as a magnetic or optical disk and its corresponding disk drive) as permanent storage device 1102.

Other implementations use a removable storage device (such as a floppy disk, flash drive, and its corresponding disk drive) as permanent storage device 1102. Like permanent storage device 1102, system memory 1104 is a read-and-write memory device. However, unlike storage device 1102, system memory 1104 is a volatile read-and-write memory, such a random access memory. System memory 1104 stores some of the instructions and data that the processor needs at runtime. In some implementations, the processes of the subject disclosure are stored in system memory 1104, permanent storage device 1102, and/or ROM 1110. From these various memory units, processing unit(s) 1112 retrieves instructions to execute and data to process in order to execute the processes of some implementations.

Bus 1108 also connects to input and output device interfaces 1114 and 1106. Input device interface 1114 enables the user to communicate information and select commands to the electronic system. Input devices used with input device interface 1114 include, e.g., alphanumeric keyboards and pointing devices (also called "cursor control devices"). Output device interfaces 1106 enables, e.g., the display of images generated by the electronic system 1100. Output devices used with output device interface 1106 include, e.g., printers and display devices, such as cathode ray tubes (CRT) or liquid crystal displays (LCD). Some implementations include devices such as a touchscreen that functions as both input and output devices.

Also, as shown in FIG. 11, bus 1108 also couples electronic system 1100 to a network (not shown) through network interfaces 1116. Network interfaces 1116 may include, e.g., a wireless access point (e.g., Bluetooth or WiFi) or radio circuitry for connecting to a wireless access point. Network interfaces 1116 may also include hardware (e.g., Ethernet hardware) for connecting the computer to a part of a network of computers such as a local area network ("LAN"), a wide area network ("WAN"), wireless LAN, or an Intranet, or a network of networks, such as the Internet. Any or all components of electronic system 1100 can be used in conjunction with the subject disclosure.

These functions described above can be implemented in computer software, firmware or hardware. The techniques can be implemented using one or more computer program products. Programmable processors and computers can be included in or packaged as mobile devices. The processes and logic flows can be performed by one or more programmable processors and by one or more programmable logic circuitry. General and special purpose computing devices and storage devices can be interconnected through communication networks.

Some implementations include electronic components, such as microprocessors, storage and memory that store computer program instructions in a machine-readable or computer-readable medium (also referred to as computer-readable storage media, machine-readable media, or machine-readable storage media). Some examples of such computer-readable media include RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, read-only and recordable Blu-Ray® discs, ultra density optical discs, any other optical or magnetic media, and floppy disks. The computer-readable media can store a computer program that is executable by at least one processing unit and includes sets of instructions for performing various operations. Examples of computer programs or computer code include machine code, such as is produced by a compiler, and files including higher-level code that are executed by a computer, an electronic component, or a microprocessor using an interpreter.

While the above discussion primarily refers to microprocessor or multi-core processors that execute software, some implementations are performed by one or more integrated circuits, such as application specific integrated circuits (ASICs) or field programmable gate arrays (FPGAs). In some implementations, such integrated circuits execute instructions that are stored on the circuit itself.

As used in this specification and any claims of this application, the terms "computer", "server", "processor", and "memory" all refer to electronic or other technological devices. These terms exclude people or groups of people. For the purposes of the specification, the terms display or displaying means displaying on an electronic device. As used in this specification and any claims of this application, the terms "computer readable medium" and "computer readable media" are entirely restricted to tangible, physical objects that store information in a form that is readable by a computer. These terms exclude any wireless signals, wired download signals, and any other ephemeral signals.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; e.g., feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; e.g., by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include clients and servers. A client and server are generally remote from each other and may interact through a communication network. The relationship of client and server arises by virtue of computer programs running on the respective computers and having a client-server relationship to each other. In some embodiments, a server transmits data (e.g., an HTML page) to a client device (e.g., for purposes of displaying data to and receiving user input from a user interacting with the client device). Data generated at the client device (e.g., a result of the user interaction) can be received from the client device at the server.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. The described functionality may be implemented in varying ways for each particular application. Various components and blocks may be arranged differently (e.g., arranged in a different order, or partitioned in a different way) all without departing from the scope of the subject technology.

It is understood that the specific order or hierarchy of steps in the processes disclosed is an illustration of example approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

Illustration of Subject Technology as Clauses

Various examples of aspects of the disclosure are described as numbered clauses (1, 2, 3, etc.) for convenience. These are provided as examples, and do not limit the subject technology. Identifications of the figures and reference numbers are provided below merely as examples and for illustrative purposes, and the clauses are not limited by those identifications.

Clause 1. A method comprising: receiving, by a control module of a patient care device, from a device remote from the control module, a new configuration package, wherein the new configuration package comprises one or more versions of firmware for at least one of the control module and a first functional module of the patient care device; storing, by the control module, the new configuration package in a first memory bank of the control module, wherein a second configuration package is stored in a second memory bank of the control module when the new configuration package is received, and wherein the second configuration package comprises a current version of firmware for at least one of the control module and the first functional module; determining, by the control module, based on information associated with the configuration package, that the new configuration package includes a new version of firmware for the first functional module connected to the control module; and based on determining that the new version of firmware is included, transmitting, by the control module, the new version of firmware to the first functional module, wherein the new version is stored on the first functional module in a different memory bank than a memory bank currently storing a firmware currently used by the first functional module.

Clause 2. The computer-implemented method of Clause 1, further comprising: receiving, by the control module, an activation command from a central computing system; determining, by the control module, in response to the activation command, whether the patient care device is currently active based on a status indicator of the patient care device; and in response to determining that the patient care device is currently inactive, switching, by the control module, execution of a current version of firmware for the control module stored in the second memory bank to a new version of firmware for the control module included in the new configuration package and stored in the first memory bank.

Clause 3. The computer-implemented method of Clause 2, further comprising: receiving, by the control module, a second activation command from the central computing system; and in response to receiving the second activation command and when the patient care device is determined to be inactive, switching, by the control module, execution of the new version of firmware for the control module stored in the first memory bank back to the version of firmware for the control module stored in the second memory bank.

Clause 4. The computer-implemented method of Clause 2, further comprising: prior to switching execution to the new version of firmware for the control module: initiating, by the control module, a power-down process of the control module in response to determining that the patient care device is currently inactive; and during a boot-up process of the control module after completion of the power-down process, initiating, by the control module, the step of switching execution to the new version of firmware for the control module.

Clause 5. The computer-implemented method of Clause 4, further comprising: during the boot-up process, detecting, by the control module, a connection to the first functional module; and sending, by the control module, in response to detecting the connection, an instruction to the first functional module to switch execution to the new version of firmware of the first functional module.

Clause 6. The computer-implemented method of Clause 1, further comprising: prior to transmitting the new version of firmware to the first functional module: determining, by the control module, based on available bandwidth of one or more processors of the control module, whether available computing resources of the control module are sufficient to transmit the new version of firmware to the first functional module; and in response to determining that the available computing resources are sufficient, initiating, by the control module, the transmitting of the new version of firmware to the first functional module.

Clause 7. The computer-implemented method of Clause 1, further comprising: determining, by the control module, whether the new configuration package includes the new version of the firmware for the first functional module based on an identifier associated with the new version of firmware for the first functional module and the first functional module.

Clause 8. The computer-implemented method of Clause 1, further comprising: detecting, by the control module, a new connection from a second functional module; and sending, by the control module, responsive to the new connection, a message to the second functional module indicating a version of firmware of the second functional module to execute on the second functional module.

Clause 9. The computer-implemented method of Clause 8, further comprising: receiving, by the control module, a response from the second functional module, wherein in the response indicates that the version of firmware indicated in the message is unavailable in the second functional module; providing, by the control module, based on the response, an alert to a user for display at a display device associated with the control module, wherein the alert indicates that the version of firmware is unavailable in the second functional module; receiving, by the control module, responsive to the alert, an input from the user to send the version of firmware to the second functional module; and sending, by the control module, based on the input, the version of firmware to the second functional module, wherein the new configuration package includes the version of the firmware for the second functional module.

Clause 10. The computer-implemented method of Clause 1, further comprising: detecting, by the control module, a new connection from a third functional module; determining, by the control module, responsive to the new connection from the third functional module, based on a message from the third functional module, whether a version of firmware executing on the third functional module is compatible with a current version of firmware executing on the control module; and in response to determining that the version of firmware is incompatible, causing, by the control module, the third functional module to execute a version of firmware of the third functional module compatible with the current version of firmware executing on the control module.

Clause 11. The computer-implemented method of Clause 10, wherein the version of firmware executing on the third functional module is stored in a first memory bank of the third functional module and a version of firmware compatible with the current version of firmware executing on the control module is stored in a second memory bank of the third functional module.

Clause 12. The computer-implemented method of Clause 10, wherein causing the third functional module to execute the version of firmware of the third functional module compatible with the current version of firmware executing on the control module, further comprises: sending an instruction to switch execution to the version of firmware stored in a second memory bank of the third functional module.

Clause 13. A patient care system comprising: a first functional module; and a control module, the control module comprising a memory and one or more processors configured to execute instructions stored on the memory to cause the control module to: receive, from a device remote from the patient care system, a new configuration package, wherein the new configuration package comprises one or more versions of firmware for at least one of the control module and the first functional module; store the new configuration package in a first memory bank of the control module, wherein a second configuration package is stored in a second memory bank of the control module when the new configuration package is received, and wherein the second configuration package comprises a current version of firmware for at least one of the control module and the first functional modules; determine, based on information associated with the new configuration package, whether the new configuration package includes a new version of firmware for the first functional module connected to the control module; and when the new version of firmware is included, transmit the new version of firmware to the first functional module, wherein the new version is stored on the first functional module in a different memory bank than a memory bank currently storing a firmware currently used by the first functional module.

Clause 14. The patient care system of Clause 13, wherein the one or more processors are configured to execute instructions to cause the control module to: receive an activation command from a central computing system; in response to the activation command, determine whether the patient care system is currently active based on a status indicator of the patient care system; and when the patient care system is currently inactive, switch execution of a current version of firmware for the control module stored in the second memory bank to a new version of firmware for the control module included in the new configuration package and stored in the first memory bank.

Clause 15. The patient care system of Clause 14, wherein the one or more processors are configured to execute instructions to cause the control module to: receive a second activation command from the central computing system; and based on the second activation command and when the patient care system is inactive, switch execution of the new version of firmware for the control module stored in the first memory bank back to the version of firmware for the control module stored in the second memory bank.

Clause 16. The patient care system of Clause 14, wherein the one or more processors are configured to execute instructions to cause the control module to: prior to switching execution to the new version of firmware for the control module: initiate a power-down process of the control module when the patient care system is currently inactive; and during a boot-up process of the control module after completion of the power-down process, switch execution to the new version of firmware for the control module.

Clause 17. The patient care system of Clause 16, wherein the one or more processors are configured to execute instructions to cause the control module to: during the boot-up process, detect a connection to the first functional module; and when the connection to the first functional module is detected, send an instruction to the first functional module to switch execution to the new version of firmware of the first functional module.

Clause 18. The patient care system of Clause 13, wherein the one or more processors are configured to execute instructions to cause the control module to: prior to transmitting the new version of firmware to the first functional module: determine, based on available bandwidth of the one or more processors of the control module, whether available computing resources of the control module are sufficient to transmit the new version of firmware to the first functional module; and when the available computing resources are sufficient, transmit the new version of firmware to the first functional module.

Clause 19. The patient care system of Clause 13, wherein the one or more processors are configured to execute instructions to cause the control module to: determine whether the new configuration package includes the new version of the firmware for the first functional module based on an identifier associated with the new version of firmware for the first functional module and the first functional module.

Clause 20. The patient care system of Clause 13, wherein the one or more processors are configured to execute instructions to cause the control module to: detect a new connection from a second functional module; and send, responsive to the new connection, a message to the second functional module indicating a version of firmware of the second functional module to execute on the second functional module.

Clause 21. The patient care system of Clause 20, wherein the one or more processors are configured to execute instructions to cause the control module to: receive a response from the second functional module, wherein in the response indicates that the version of firmware indicated in the message is unavailable in the second functional module; provide, based on the response, an alert to a user for display at a display device associated with the control module, wherein the alert indicates that the version of firmware is unavailable in the second functional module; receive, responsive to the alert, an input from the user to send the version of firmware to the second functional module; and send, based on the input, the version of firmware to the second functional module, wherein the new configuration package includes the version of the firmware for the second functional module.

Clause 22. The patient care system of Clause 13, wherein the one or more processors are configured to execute instructions to cause the control module to: detect a new connection from a third functional module; determine, responsive to the new connection from the third functional module, based on a message from the third functional module, whether a version of firmware executing on the third functional module is compatible with a current version of firmware executing on the control module; and when the version of firmware is incompatible, cause the third functional module to execute a version of firmware of the third functional module compatible with the current version of firmware executing on the control module.

Clause 23. The patient care system of Clause 22, wherein the version of firmware executing on the third functional module is stored in a first memory bank of the third functional module and a version of firmware compatible with the current version of firmware executing on the control module is stored in a second memory bank of the third functional module.

Clause 24. The patient care system of Clause 22, wherein the one or more processors are configured to execute instructions to cause the control module to: send an instruction to switch execution to the version of firmware stored in a second memory bank of the third functional module to cause the third functional module to execute the version of firmware of the third functional module compatible with the current version of firmware executing on the control module.

Clause 25. The patient care system of Clause 13, wherein the new versions of the firmware include respective instructions for adjusting a functional module based on a predefined parameter, and wherein the new configuration package includes drug library information including the predefined parameter, and wherein the current version of the firmware ignores the predefined parameter.

Clause 26. The patient care system of Clause 13, wherein the first functional module comprises a fluid pump module, and wherein the firmware includes instructions to control a flow rate for the fluid pump module.

Clause 27. The patient care system of Clause 13, wherein the first functional module comprises a syringe pump module, and wherein the firmware includes instructions to control pressure applied to a syringe received by the syringe pump module.

Clause 28. A non-transitory machine readable medium comprising instructions stored thereon that, when executed by a device, cause the device to perform operations comprising: receiving, by a control module of a patient care device, from a device remote from the control module, a new configuration package, wherein the new configuration package comprises one or more versions of firmware for at least one of the control module and a first functional module of the patient care device; storing, by the control module, the new configuration package in a first memory bank of the control module, wherein a second configuration package is stored in a second memory bank of the control module when the new configuration package is received, and wherein the second configuration package comprises a current version of firmware for at least one of the control module and the first functional module; determining, by the control module, based on information associated with the configuration package, that the new configuration package includes a new version of firmware for the first functional module connected to the control module; and responsive to determining that the new version of firmware is included, transmitting, by the control module, the new version of firmware to the first functional module, wherein the new version is stored on the first functional module in a different memory bank than a memory bank currently storing a firmware currently used by the first functional module.

Further Consideration

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention described herein.

The term website, as used herein, may include any aspect of a website, including one or more web pages, one or more servers used to host or store web related content, etc. Accordingly, the term website may be used interchangeably with the terms web page and server. The predicate words "configured to", "operable to", and "programmed to" do not imply any particular tangible or intangible modification of a subject, but, rather, are intended to be used interchangeably. For example, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

The term automatic, as used herein, may include performance by a computer or machine without user intervention; for example, by instructions responsive to a predicate action by the computer or machine or other initiation mechanism. The word "example" is used herein to mean "serving as an example or illustration." Any aspect or design described herein as "example" is not necessarily to be construed as preferred or advantageous over other aspects or designs.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such as an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

What is claimed is:

1. A computer-implemented method, comprising:
   receiving, by a control module of a patient care device, from a device remote from the control module, a new configuration package, wherein the new configuration package comprises a first module firmware for a first type of infusion device module connected to the control module, and a second module firmware for a second type of infusion device module connected to the control module;
   receiving information associated with the new configuration package, the received information identifying a version of the first module firmware and specifying that the first module firmware is for the first type of infusion device module and identifying a version of the second module firmware and specifying that the second module firmware is for the second type of infusion device module, the first type and the second type of infusion device module each being a large volume infusion pump or a syringe pump;
   storing, by the control module, the received new configuration package in a first memory bank of the control module, wherein a second configuration package is stored in a second memory bank of the control module when the new configuration package is received;
   determining, by the control module, based on the information associated with the new configuration package, received by the control module from the remote device and stored in the first memory bank of the control module, that a first infusion device module connected to the control module is of the first type specified by the received information and that the identified version of the first module firmware is a new version for the first infusion device module connected to the control module, or that a second infusion device module connected to the control module is of the second type specified by the received information and that the identified version of the second module firmware is a new version for the second infusion device module connected to the control module;
   responsive to determining that the first infusion device module is the first type specified by the received information and the first module firmware is a new version for the first infusion device module or the second infusion device module is the second type specified by the received information and the second module firmware is a new version for the second infusion device module, and that the first infusion device module or the second infusion device module, respectively, is connected to the control module:
   transmitting, by the control module, the corresponding module firmware to a first memory bank of the connected infusion device module while a current version of the firmware for the connected infusion device module is stored in a second memory bank of the connected infusion device module that is different than the first memory bank of the connected infusion device module, wherein the current version of the firmware for the connected infusion device module is currently used by the connected infusion device module while being stored in the second memory bank of the connected infusion device module and while the corresponding module firmware received from the remote device is being transmitted to the first memory bank of the connected infusion device module.

2. The computer-implemented method of claim 1, wherein the patient care device is associated with a predetermined configuration zone, and the new configuration package is received from the remote device based on the patient care device being within the predetermined configuration zone, wherein the predetermined configuration zone comprises a geographic location or care area, the method further comprising:
   receiving, by the control module, an activation command from a central computing system based on the patient care device being within the predetermined configuration zone;
   determining, by the control module, in response to the activation command, whether the patient care device is currently active based on a status indicator of the patient care device; and
   in response to determining that the patient care device is currently inactive, by the control module, sending the connected infusion device module an instruction to switch execution of the current version of the firmware stored in the second memory bank of the connected infusion device module to the corresponding module firmware stored in the first memory bank of the connected infusion device module.

3. The computer-implemented method of claim 1, further comprising:
   receiving, by the control module, an indication from the connected infusion device module that the corresponding module firmware was successfully stored in the first memory bank of the connected infusion device module; and in response to receiving the indication, by the control module, sending the connected infusion device module an instruction to switch execution of the current version of the firmware for the connected infusion device module stored in the second memory bank of the connected infusion device module to the corresponding module firmware stored in the first memory bank of the connected infusion device module.

4. The computer-implemented method of claim 3, further comprising:

prior to switching execution to the corresponding module firmware for the connected infusion device module:

initiating, by the control module, a power-down process of the control module in response to determining that the patient care device is currently inactive; and during a boot-up process of the control module after completion of the power-down process, initiating, by the control module, the step of switching execution to the corresponding module firmware for the connected infusion device module.

5. The computer-implemented method of claim 1, further comprising:

during a boot-up process, detecting, by the control module, a connection to the connected infusion device module; and sending, by the control module, in response to detecting the connection, an instruction to the connected infusion device module to switch execution to the corresponding module firmware of the connected infusion device module.

6. The computer-implemented method of claim 1, further comprising:

prior to transmitting the corresponding module firmware to the connected infusion device module:

determining, by the control module, based on available bandwidth of one or more processors of the control module, whether available computing resources of the control module are sufficient to transmit the corresponding module firmware to the connected infusion device module; and in response to determining that the available computing resources are sufficient, initiating, by the control module, the transmitting of the corresponding module firmware to the connected infusion device module.

7. The computer-implemented method of claim 1, further comprising:

determining, by the control module, whether the new configuration package includes the corresponding module firmware for the connected infusion device module based on an identifier associated with the corresponding module firmware for the connected infusion device module.

8. The computer-implemented method of claim 1, further comprising:

detecting, by the control module, a new connection from the second infusion device module; and sending, by the control module, responsive to the new connection, a message to the second infusion device module indicating a version of firmware of the second infusion device module to execute on the second infusion device module.

9. The computer-implemented method of claim 8, further comprising:

receiving, by the control module, a response from the second connected infusion device module, wherein in the response indicates that the version of firmware indicated in the message is unavailable in the second connected infusion device module;

providing, by the control module, based on the response, an alert to a user for display at a display device associated with the control module, wherein the alert indicates that the version of firmware is unavailable in the second connected infusion device module;

receiving, by the control module, responsive to the alert, an input from the user to send the version of firmware to the second connected infusion device module; and sending, by the control module, based on the input, the version of firmware to the second connected infusion device module, wherein the new configuration package includes the version of the firmware for the second connected infusion device module.

10. The computer-implemented method of claim 1, further comprising:

detecting, by the control module, a new connection from a functional module;

determining, by the control module, responsive to the new connection from the functional module, based on a message from the functional module, whether a version of firmware executing on the functional module is compatible with a version of firmware executing on the control module; and in response to determining that the version of firmware executing on the functional module is incompatible, causing, by the control module, the functional module to execute a version of firmware of the functional module compatible with the version of firmware executing on the control module.

11. The computer-implemented method of claim 10, wherein the version of firmware executing on the functional module is stored in a first memory bank of the functional module and a version of firmware compatible with the current version of firmware executing on the control module is stored in a second memory bank of the functional module.

12. The computer-implemented method of claim 10, wherein causing the functional module to execute the version of firmware of the functional module compatible with the current version of firmware executing on the control module, further comprises:

sending an instruction to switch execution to the version of firmware stored in a second memory bank of the functional module.

13. A patient care system comprising:

a first infusion device module; and a control module operably connected to the first infusion device module, the control module comprising a memory and one or more processors configured to execute instructions stored on the memory to cause the control module to:

receive, from a device remote from the patient care system, a new configuration package, wherein the new configuration package comprises a first module firmware for a first type of infusion device module, and a second module firmware for a second type of infusion device module connected to the control module;

receive information associated with the new configuration package, the received information identifying a version of the first module firmware and specifying that the first module firmware is for the first type of infusion device module and identifying a version of the second module firmware and specifying that the second module firmware is for the second type of infusion device module, the first type and the second type of infusion device module each being a large volume infusion pump or a syringe pump;

store the received new configuration package in a first memory bank of the control module, wherein a second configuration package is stored in a second memory bank of the control module when the new configuration package is received;

determine, based on information associated with the received new configuration package, received from the remote device and stored in the first memory bank of the control module, that the first infusion device module connected to the control module is of the first type specified by the received information and that the identified version of the first module firmware is a new version for the first infusion device module connected to the control module, or that a second infusion device module-connected to the control module is of the second type specified by the received information and that the identified version of the second module firmware is a new version for the second infusion device module connected to the control module;

responsive to determining that the first infusion device module is the first type specified by the received information and the first module firmware is a new version for the first infusion device module or the second infusion device module is the second type specified by the received information and the second module firmware is a new version for the second infusion device module, and that the first infusion device module or the second infusion device module, respectively, is connected to the control module:

transmit the corresponding module firmware to a first memory bank of the connected infusion device module while a current version of the firmware for the connected infusion device module is stored in a second memory bank of the connected infusion device module that is different than the first memory bank of the connected infusion device module, wherein the current version of the firmware for the connected infusion device module is currently used by the connected infusion device module while being stored in the second memory bank of the connected infusion device module and while the corresponding module firmware received from the remote device is being transmitted to the first memory bank of the connected infusion device module.

14. The patient care system of claim 13, wherein the patient care device is associated with a predetermined configuration zone, and the new configuration package is received from the remote device based on the patient care device being within the predetermined configuration zone, wherein the predetermined configuration zone comprises a geographic location or care area, wherein the one or more processors are configured to execute instructions to cause the control module to:

receive an activation command from a central computing system, wherein the activation command is received based on the patient care device being within the predetermined configuration zone;

in response to the activation command, determine whether the patient care system is currently active based on a status indicator of the patient care system; and when the patient care system is currently inactive, sending the connected infusion device module an instruction to switch execution of the current version of firmware stored in the second memory bank of the connected infusion device module to the corresponding module firmware stored in the first memory bank of the connected infusion device module.

15. The patient care system of claim 13, wherein the one or more processors are configured to execute instructions to cause the control module to:

receive an indication from the connected infusion device module that the corresponding module firmware was successfully stored in the first memory bank of the connected infusion device module; and based on the indication, switch execution of the current version of the firmware for the connected infusion device module stored in the second memory bank of the connected infusion device module to the corresponding module firmware stored in the first memory bank of the connected infusion device module.

16. The patient care system of claim 15, wherein the one or more processors are configured to execute instructions to cause the control module to:

prior to switching execution to the corresponding module firmware for the connected infusion device module:
    initiate a power-down process of the control module when the patient care system is currently inactive; and
    during a boot-up process of the control module after completion of the power-down process, switch execution to the corresponding module firmware for the connected infusion device module.

17. The patient care system of claim 13, wherein the one or more processors are configured to execute instructions to cause the control module to:

during a boot-up process, detect a connection to the connected infusion device module; and when the connection to the connected infusion device module is detected, send an instruction to the first infusion device module to switch execution to the corresponding module firmware of the connected infusion device module.

18. The patient care system of claim 13, wherein the one or more processors are configured to execute instructions to cause the control module to:

prior to transmitting the corresponding module firmware to the connected infusion device module:
    determine, based on available bandwidth of the one or more processors of the control module, whether available computing resources of the control module are sufficient to transmit the corresponding module firmware to the connected infusion device module; and
    when the available computing resources are sufficient, transmit the corresponding module firmware to the connected infusion device module.

19. The patient care system of claim 13, wherein the one or more processors are configured to execute instructions to cause the control module to:

determine whether the new configuration package includes the corresponding module firmware for the connected infusion device module based on an identifier associated with the corresponding module firmware for the connected infusion device module.

20. The patient care system of claim 13, wherein the one or more processors are configured to execute instructions to cause the control module to:

detect a new connection from a functional module; and send, responsive to the new connection, a message to the functional module indicating a version of firmware of the functional module to execute on the functional module.

21. The patient care system of claim 20, wherein the one or more processors are configured to execute instructions to cause the control module to:

receive a response from the functional module, wherein in the response indicates that the version of firmware indicated in the message is unavailable in the functional module;

provide, based on the response, an alert to a user for display at a display device associated with the control module, wherein the alert indicates that the version of firmware is unavailable in the functional module;

receive, responsive to the alert, an input from the user to send the version of firmware to the functional module; and send, based on the input, the version of firmware to the functional module, wherein the new configuration package includes the version of the firmware for the functional module.

22. The patient care system of claim 13, wherein the one or more processors are configured to execute instructions to cause the control module to:

detect a new connection from a functional module associated with the control module;

determine, responsive to the new connection from the functional module, based on a message from the functional module, whether a version of firmware executing on the functional module is compatible with a version of firmware executing on the control module; and when the version of firmware executing on the functional module is incompatible, cause the functional module to execute a version of firmware of the functional module compatible with the version of firmware executing on the control module.

23. The patient care system of claim 22, wherein the version of firmware executing on the functional module is stored in a first memory bank of the functional module and a version of firmware compatible with the current version of firmware executing on the control module is stored in a second memory bank of the functional module.

24. The patient care system of claim 22, wherein the one or more processors are configured to execute instructions to cause the control module to:

send an instruction to switch execution to the version of firmware stored in a second memory bank of the functional module to cause the functional module to execute the version of firmware of the functional module compatible with the current version of firmware executing on the control module.

25. The patient care system of claim 13, wherein the corresponding module firmware includes respective instructions for adjusting a functional module based on a predefined parameter, and wherein the new configuration package includes drug library information including the predefined parameter, and wherein the current version of the firmware ignores the predefined parameter.

26. The patient care system of claim 13, wherein the first infusion device module comprises a fluid pump module, and wherein the firmware includes instructions to control a flow rate for the fluid pump module.

27. The patient care system of claim 13, wherein the second infusion device module comprises a syringe pump module, and wherein the firmware includes instructions to control pressure applied to a syringe received by the syringe pump module.

28. A non-transitory machine readable medium comprising instructions stored thereon that, when executed by a device, cause the device to perform operations comprising:

receiving, by a control module of a patient care device, from a device remote from the control module, a new configuration package, wherein the new configuration package comprises a first module firmware for a first type of infusion device module connected to the control module, and a second module firmware for a second type of infusion device module connected to the control module;

receiving information associated with the new configuration package, the received information identifying a version of the first module firmware and specifying that the first module firmware is for the first type of infusion device module and identifying a version of the second module firmware and specifying that the second module firmware is for the second type of infusion device module, the first type and the second type of infusion device module each being a large volume infusion pump or a syringe pump;

storing, by the control module, the received new configuration package in a first memory bank of the control module, wherein a second configuration package is stored in a second memory bank of the control module when the new configuration package is received;

determining, by the control module, based on information associated with the new configuration package, received by the control module from the remote device and stored in the first memory bank of the control module, that a first infusion device module connected to the control module is of the first type specified by the received information and that the identified version of the first module firmware is a new version for the first infusion device module connected to the control module, or that a second infusion device module connected to the control module is of the second type specified by the received information and that the identified version of the second module firmware is a new version for the second infusion device module connected to the control module;

responsive to determining that the first infusion device module is the first type specified by the received information and the first module firmware is a new version for the first infusion device module or the second infusion device module is the second type specified by the received information and the second module firmware is a new version for the second infusion device module, and that the first infusion device module or the second infusion device module, respectively, is connected to the control module:

transmitting, by the control module, the corresponding module firmware to a first memory bank of the connected infusion device module while a current version of the firmware for the connected infusion device module is stored in a second memory bank of the connected infusion device module that is different than the first memory bank of the connected infusion device module, wherein the current version of the firmware for the connected infusion device module is currently used by the connected infusion device module while being stored in the second memory bank of the connected infusion device module and while the corresponding module firmware received from the remote device is being transmitted to the first memory bank of the connected infusion device module.

\* \* \* \* \*